United States Patent [19]
Kato et al.

[11] Patent Number: 6,096,530
[45] Date of Patent: Aug. 1, 2000

[54] *PSEUDOMONAS CEPACIA* STRAIN ISOLATED FROM TERMITE INTESTINES THAT DEGRADES TRICHLORETHYLENE AND FURAN COMPOUNDS

[75] Inventors: Kinya Kato, Atsugi; Shinya Kozaki, Sakurashin-machi; Takeshi Imamura, Chigasaki; Masanori Sakuranaga, Atsugi, all of Japan

[73] Assignee: Canon Kabushiki Kaisha, Tokyo, Japan

[21] Appl. No.: 08/810,366

[22] Filed: Mar. 3, 1997

Related U.S. Application Data

[63] Continuation-in-part of application No. 08/707,497, Sep. 24, 1996, abandoned, which is a continuation of application No. 08/608,966, Feb. 29, 1996, abandoned, which is a continuation of application No. 08/138,031, Oct. 19, 1993, abandoned, and a continuation of application No. 08/778,680, Jan. 3, 1997, abandoned, which is a continuation of application No. 08/352,442, Dec. 9, 1994, abandoned, which is a continuation of application No. 08/048,524, Apr. 20, 1993, abandoned.

[30]  Foreign Application Priority Data

| Apr. 22, 1992 | [JP] | Japan | 4-103180 |
| Jul. 31, 1992 | [JP] | Japan | 4-204913 |
| Feb. 18, 1993 | [JP] | Japan | 5-29316 |
| Feb. 18, 1993 | [JP] | Japan | 5-29317 |
| Oct. 18, 1993 | [JP] | Japan | 5-259741 |

[51] Int. Cl.$^7$ .................................................. C12N 1/20
[52] U.S. Cl. ................................. 435/253.3; 435/252.1; 435/34
[58] Field of Search ................................. 435/252.1, 34, 435/172.1, 253.3, 170

[56]  References Cited

U.S. PATENT DOCUMENTS

| 4,266,030 | 5/1981 | Tschang et al. | 435/180 |
| 4,456,685 | 6/1984 | Guthrie | 435/109 |
| 4,535,061 | 8/1985 | Chakrabarty | 435/253 |
| 4,556,623 | 12/1985 | Tamura et al. | 430/83 |
| 4,859,594 | 8/1989 | Portier | 435/172.1 |
| 4,871,673 | 10/1989 | Rehm et al. | 435/262 |
| 4,877,736 | 10/1989 | Fiermans | 435/183 |
| 4,925,802 | 5/1990 | Nelson et al. | 435/262 |
| 5,202,227 | 4/1993 | Matsuda et al. | 430/320 |
| 5,219,926 | 6/1993 | Linman et al. | 525/54.1 |
| 5,284,587 | 2/1994 | Wong et al. | 210/606 |
| 5,294,491 | 3/1994 | Goeldner et al. | 428/402 |

FOREIGN PATENT DOCUMENTS

| 090652 | 10/1983 | European Pat. Off. . | |
| 095049 | 11/1983 | European Pat. Off. . | |
| 0567102 | 10/1993 | European Pat. Off. . | |
| 2501229 | 10/1992 | France . | |
| 2752380 | 5/1979 | Germany . | |
| 3613575 | 10/1987 | Germany . | |
| 20389 | 9/1969 | Japan . | |
| 2-92274 | 4/1990 | Japan | C12N 1/20 |
| 3-292970 | 12/1991 | Japan | A62D 3/00 |
| 90-01465 | 2/1990 | WIPO . | |
| 90-10079 | 7/1990 | WIPO . | |
| 92/19738 | 11/1992 | WIPO . | |

OTHER PUBLICATIONS

Kato et al., Biotechnol. Lett. (1998), 20(5), 459–462.
Masque et al., Biotechnol. Lett. (1987), 9(9), 655–660.
French et al., Mater. Org. (Berl.), 16(4), pp. 281–288, 1975.
French, J., Material und. Organismen 10 (1) (1975), pp. 1–13.
Gibson, et, al., "Oxidative Degradation . . . ", Biochem., Col. 7, No. 7, Jul. 1968, pp. 2653–2662.
Whitenbury, et, al., "Enrichment, Isolation . . . ", J. Gen. Microbiol., vol. 61, Part 2, May 1970, pp. 205–218.
Dakin et al., "Lactobacilli Causing Spoilage . . . ", J. Appl. Bact., vol. 34, No. 3. pp. 541–545, Sep. 1971.
Beam et al., "Microbial Degradation . . . ", J. Gen. Microbiol, vol. 82, Part 1, pp. 163–169, May 1974.
Nelson et, al., "Aerobic Metabolism . . . ", Appl. & Envir. Microbiol., vol. 52, No. 2, pp. 383–384, Aug. 1986.
Wackett et, al., "Degradation of Trichloroethylene . . . ", Appln. & Envir. Microbiol., vol. 54, No. 7, pp. 1703–1708, Jul. 1988.
Journal of Japan Works Association, vol. 24, No. 273, pp. 27–33 (1987) and English Trans. of Article.
Vanderbergh, et al., "Metabolism of Volitile . . . ", Appl. & Environ. Microbiol., vol. 54, No. 10, pp. 2578–2579, Oct. 1988.
Arciero, et al., "Degradation of Trichloroethylene . . . ", Biochem. & Biophys. Res. Comm., vol. 159, No. 2, pp. 640–643, Mar. 1989.
Embley, et al., "Lactobacillus Vaginalis . . . ", Int. Journ. System Bacter., vol. 39, No. 3, pp. 368–370, Jul. 1989.
Wacket, et al., "Survey of Microbial Oxygenases . . . ", Appl. & Environ. Microbial., vol. 55, No. 11, pp. 2960–2964, Nov. 1989.

(List continued on next page.)

*Primary Examiner*—Irene Marx
*Attorney, Agent, or Firm*—Fitzpatrick, Cella, Harper & Scinto

[57]  ABSTRACT

A biologically pure culture of *Pseudomonas cepacia* strain KK01 (FERM BP-4235) is capable of degrading trichloroethylene. A method for obtaining microorganisms having a trichloroethylene degrading ability comprises the steps of culturing microorganisms separated from the bodies of termites in a culture medium. A method for remediating a soil contaminated with trichloroethylene comprises the steps of providing a soil contaminated with trichloroethylene and bringing microorganisms having a trichloroethylene degrading ability derived from intestine of termites into contact with the soil, and biodegrading trichloroethylene in the soil. A method for biodegrading trichloroethylene, comprises the steps of culturing *Pseudomonas cepacia* KK01 (FERM BP-4235) under existence of an inducer and inducing *Pseudomonas cepacia* KK01 (FERM BP-4235) to have ability for degrading trichloroethylene and bringing *Pseudomonas cepacia* KK01 having trichloroethylene degrading ability to contact with trichloroethylene and biodegrading trichloroethylene.

4 Claims, 26 Drawing Sheets

OTHER PUBLICATIONS

Harker et al., "Trichloroethylene Degradation . . . ", Appl. & Environ. Microbiol., vol. 56, No. 4, pp. 1179–1181, Apr. 1990.

Folsom et al., "Phenol & Trichloroethylene . . . ", Appl. & Environ. Microbiol., vol. 56, No. 5, pp. 1279–1285, May 1990.

Ewers et al., "Selection of Trichloroethene . . . ", Arch. Microbiol., vol. 154, No. 4, 410–413, 1990.

Henry et al., "Influence of Endogenous . . . ", Appl. & Environ. Microbiol., vol. 57, No. 1, pp. 236–244, Jan. 1991.

Morimoto, et al. J. Ferm. Techn., vol. 45, No. 442 (1967).

Skryabin, et al., "Conversion of Organic Compound by Microorganism" translated by S. Fukui, 287.

Brune, et al., Process Biochem, vol. 17, No. 20 (1982).

Kunkee, et al., Int. J. Syst. Bact., vol. 30, pp. 313–314 (1980).

Shields, et al., Mutants of Pseudonyms . . . and Trichloroethylene, Appl. & Envr. Microb., vol. 57, No. 7 (1991) pp. 1935–1941.

French, et al, Lignin . . . Mater. Org., vol. 10, (4), pp. 281–288 (1975).

Lee, K.E., et al. "Termites & Soils"; Publishers Academic Press, pp. 128–145 (1971).

O'Brien, et al. "Role of Microorganisms . . . Termites", Aust. J. Biol. Sci., vol. 35, pp. 239–262 (1982).

Lee, M.J., et al. "Association of . . . Hindgut", *Current Microbiology*, vol. 15, (1987), pp. 337–341.

Odelson, et ala. "Nutrition . . . from Termites", Appl. of Environ. Microb., vol. 49, No. 3, pp. 614–621 (1985).

Database WP1, Week 9151, Derwent Public. AN 91–373416 for JP3–251178.

Stone, et al., "A Structural Model . . . Macromolecules", Cellulose Chemistry and Technology, vol. 2, pp. 343–358 (1968).

DAYS OF CULTURE (DAY)

INFLUENCE OF PHENOL CONC. ON
GROWTH OF STRAIN KK01 (TCE CONC.: 1ppm)

INFLUENCE OF PHENOL CONC. ON
TCE DEGRADATION BY STRAIN KK01
(TCE CONC.: 5ppm)

INFLUENCE OF PHENOL CONC. ON
GROWTH OF STRAIN KK01 (TCE CONC.: 5ppm)

INFLUENCE OF PHENOL CONC. ON
TCE DEGRADATION BY STRAIN KK01
(TCE CONC.: 30ppm)

INFLUENCE OF PHENOL CONC. ON
GROWTH OF STRAIN KK01 (TCE CONC.: 30ppm)

INFLUENCE OF PHENOL CONC. ON
TCE DEGRADATION BY NATIVE BACTERIA
(TCE CONC.: 10ppm)

INFLUENCE OF PHENOL CONC. ON
GROWTH OF NATIVE BACTERIA
(TCE CONC.: 10ppm)

INFLUENCE OF PHENOL CONC. ON
cis-1, 2-DCE DEGRADATION BY STRAIN KK01

INFLUENCE OF PHENOL CONC. ON
GROWTH OF STRAIN KK01
(SUBSTANCE TO BE DEGRADED: cis-1, 2-DCE, 13ppm)

INFLUENCE OF p-CRESOL CONC. ON
TCE DEGRADATION BY STRAIN KK01
(TCE CONC.: 15ppm)

INFLUENCE OF p-CRESOL CONC. ON
GROWTH OF STRAIN KK01
(TCE CONC.: 15ppm)

INFLUENCE OF PHENOL CONC. ON GROWTH OF
AND TCE DEGRADATION BY P. PUTIDA STRAIN BH
(TCE CONC.: 5ppm)

PSEUDOMONAS CEPACIA STRAIN ISOLATED FROM TERMITE INTESTINES THAT DEGRADES TRICHLORETHYLENE AND FURAN COMPOUNDS

This is a continuation-in-part of a continuing application Ser. No. 08/707,497 filed on Sep. 24, 1996 of a prior continuing application Ser. No. 08/608,966 filed on Feb. 29, 1996 now abandoned of a prior application Ser. No. 08/138, 031 filed on Oct. 19, 1993, now abandoned and of a continuing application Ser. No. 08/778,680 filed on Jan. 3, 1997 now abandoned of a prior continuing application Ser. No. 08/352,442 filed on Dec. 9, 1994 now abandoned of a prior application Ser. No. 08/048,524 filed on Apr. 20, 1993 now abandoned.

BACKGROUND OF THE INVENTION

1. Field of the Invention

The present invention relates to a novel strain of microorganism, a method of biodegrading chemical compounds, such as trichloroethylene, phenolic compounds and furan compounds by using thereof, a method of remedying environment such as sewage, waste water, soil and so on. The present invention also relates to a method of producing 2-furan carboxylic acid from furfural biologically.

2. Related Background Art

In recent years, various environmental inspections have reported that harmful and less degradable aromatic chemical substances have been detected, and in consequence, much attention has now been paid to environmental pollution with these substances. The influence of these substances on ecological systems is feared.

Therefore, in order to prevent pollution with these less degradable chemical substances, it is required to rapidly develop a technique by which these substances are inhibited from getting into the environment. For example, it is strongly desired to establish a technique by which the less degradable harmful substances can be effectively removed from sewage or waste water. Furthermore, the pollution of a soil with the less degradable harmful substances not only hinders the reutilization of the soil but also causes further escalation of the pollution due to the running of the pollutant into groundwater, which is a serious social problem. Therefore, it is strongly desired to establish a technique by which the escalation of the pollution with the less degradable chemical substances can be prevented and the polluted environment can be remediated.

Examples of such non-decomposable substances include phenolic compounds such as phenol and cresol; furan compounds such as furfural, tetrahydrofuran, furfuryl alcohol, and cumaran.

Although phenol found in various waste liquids can be decomposed by a chemical decomposition method using light, heat, ozone or the like, microbial decomposition attracts attention from the viewpoints of treatment cost, and operation. Examples of microorganisms known as having the ability to decompose phenol include bacteria belonging to Pseudomonas, Nocardia, Bacillus, Acinetobacter, Aureobasidium; fungi belonging to Fusarium and the like; yeasts belonging to Triccosporon, Candida and the like. Typical examples of bacteria belonging to the Pseudomonas include *Pseudomonas putida,* and *Pseudomonas paucimobilis.* The Pseudomonas is now also known as Burkholderia.

Cresol is found in waste liquids of coal gasification factories, groundwater contaminated with gasoline, waste liquids of petroleum refineries and the like. The purification of such waste liquids by decomposing cresol becomes a critical problem from the viewpoint of environmental protection. Although cresol can also be decomposed by a chemical decomposition method using light, heat, ozone or the like, microbial decomposition is appreciated from the viewpoints of treatment cost and operation. However, there is substantially no isolated microorganism having the ability to decompose cresol, and only a few bacteria belonging to Pseudomonas such as Pseudomonas QT31 strain (C. Masque et al., Biotechnology Letters, Vol. 9, No. 9, 655–660, 1987) and the like are reported as cresol resistant strains.

There are only a few reports on isolated microorganisms having the ability to decompose furfural or tetrahydrofuran. Such reports include a report on decomposition of furfural by culturing bread yeasts (S. Morimoto et al., J. Ferment. Technol., 45, 442, 1967), and a former Soviet patent (Japanese Patent Publication No. 44-20389) on conversion of furfural to 2-furan carboxylic acid by Acetobacter, Achromobacter, Brevibacterium, Flavobacterium, Micrococcus or the like (refer to Conversion of Organic Compound by Microorganism, by G. K. Skryabin and L. A. Golovleva, translated by Saburo Fukui, Gakkai Shuppan Center, 287). An experiment performed under anaerobic conditions is described in Brune, G., Schovert h, S. M., and Sahm, H. (1982); Process Biochem., 17, 20. There is substantially no example of isolated microorganisms having the ability to decompose tetrahydrofuran or cumaran.

There is, thus, a great demand for practical reasons for obtaining microorganisms having the ability to decompose such non-decomposable furan compounds. As is common to aldehydes, furfural among these furan compounds has high toxicity. Thus, it is important to obtain microorganisms having resistance to the toxicity of furfural. In addition, in treatment of a compound having a cumaran ring as a basic skeleton thereof, microorganisms having the ability to decompose the cumaran ring is useful and is, therefor in great demand.

On the other hand, 2-furan carboxylic acid among the furan compounds has lower toxicity than that of furfural and is easily assimilated by microorganisms. It is to be expected that the conversion of furfural available at low cost and furan compounds mixed in various waste liquids to 2-furan carboxylic acid promotes the utilization of furan compounds in the fermentation industry.

In particular, the oxidative conversion of furfural to 2-furan carboxylic acid is a very significant means for decreasing the toxicity of furfural and introducing it as a raw material into the fermentation industry. Known methods of converting furfural to 2-furan carboxylic acid include various methods using chemical reactions. However, any one of the methods requires violent reaction, and produces high concentrations of various toxic substances in the final reaction solutions which inhibit the growth of microorganisms. When the 2-furan carboxylic acid obtained by the chemical method is used as a raw material for fermentation, it requires a troublesome operation of separating the toxic substances from the final reaction solution. From this viewpoint, attention is paid to a method of producing 2-furan carboxylic acid by using microorganisms to obtain a target substance under very mild conditions.

However, as described above, there are only a few reports on isolated microorganisms used for converting furfural to 2-furan carboxylic acid. There is, thus, a demand to obtain practical useful microorganisms.

Furfural can easily be obtained, for example, by steam distillation of a plant containing pentosan or treatment thereof with a mineral acid, and is industrially produced from hulls of oats or wheat straws. Of the furan compounds, furfural is available at the lowest cost and is widely used as a selective purification solvent for lubricating oil, a vulcanization accelerator, a dye penetrating agent and the like.

Tetrahydrofuran is useful as an organic solvent having excellent dissolving ability and is widely used as a solvent component for surface coating, an adhesive, a paint release agent and the like. Furfuryl alcohol is used as a solvent or a dispersant for dyes, phenolic resins, and a lubricant. A compound having a cumaran (2,3-dihydrobenzofuran) ring is widely used for production of dyes and pigments, as an organic solvent. The compound is also found as a component of wood.

The above compounds are thus mixed in waste liquids of various chemical factories, and the presence of tetrahydrofuran presents the danger of contaminating groundwater and the like because of water solubility. Accordingly, it is important from the viewpoint of environmental protection to decompose these compounds.

Although the non-decomposable compounds can be decomposed by a method using light, heat, ozone or the like, a biological decomposition method employing a microorganism is appreciated from the viewpoint of cost and operation properties.

There are known microorganisms having the ability to decompose phenolic compounds which include the above strains. However, satisfactory strains which satisfy practical conditions and have a sufficient decomposing ability when used for decomposing a phenolic compound using microorganisms are not found in the currently known strains. It is thus necessary to obtain a strain which satisfies the characteristics required for practical use.

In addition, only few microorganisms are known as microorganisms having the ability to decompose furan compounds which are not easily decomposed under natural conditions, and strains which satisfy practical conditions and have the sufficient decomposing ability are not currently known. Therefore, it is necessary to obtain a strain which satisfies the characteristics required for practical use.

Similarly, satisfactory microorganisms which are employed for producing 2-furan carboxylic acid from a furan compound are not found, and it is necessary to obtain a strain which satisfies the characteristics required for practical use.

The characteristics required for practical use are as follows: (1) A strain must have the ability to decompose a phenolic compound or a furan compound or the ability to convert a furfural compound to 2-furan carboxylic acid; (2) A broader range of growth conditions than those of known strains; (3) The applicability can be increased, or a strain can be utilized in various forms.

For example, microorganisms used for treating a waste water containing a phenolic compound or a furan compound are required not to be damaged easily in the waste water, necessitating microorganisms that can be grown under poor conditions, as in waste water. Microorganisms having resistance to many antibiotics and the ability to utilize various kinds of sugar have a greater possibility to grown well under poor environmental conditions. It is thus important to obtain microorganisms having resistance to various chemicals, as well as high utilization of sugar.

At an actual contamination site, composite contamination is frequently produced by several chemical substances rather than a single chemical substance. A treatment method using different kinds of bacteria for decomposing the respective chemical substances causes a problem with respect to differences in the growth conditions of the bacteria used and requires more complicated control. There is thus a demand for microorganisms of a single strain having the ability to decompose several chemical substances.

Another example of non-decomposable substance is trichloroethylene (TCE). TCE is a chlorinated organic compound which has been used in IC industries, dry cleaning and the like, and it is a carcinogen. Thus, the environmental pollution with TCE inclusive of the problem of the soil pollution caused by the pollution of groundwater is a serious social problem. Accordingly, the removal and the degradation of TCE contained in the environment, the purification of sewage or waste water containing TCE, and the remediation of the polluted soil are important themes from the viewpoint of environmental protection.

As a removal treatment and a degradation treatment of TCE, there are an adsorption treatment using active carbon, a degradation treatment utilizing light or heat, and the like. However, a biodegradation treatment using microorganisms is attracting attention from the standpoints of cost and operability.

There is a technique by which the function of microorganisms in a soil is utilized to degrade pollutants in the soil and to thereby eliminate the environmental pollution, and this technique is called bioremediation, because of remediating the soil by the use of the microorganisms. Hence, it can be expected that the bioremediation technique is applied to the remediation of polluted soils such as the vacant lot of a semiconductor manufacturing factory, a site of a metal processing factory, the vacant lot of a chemical plant, and the like.

However, there are not a many of reports that microorganisms having a TCE degrading ability have been isolated. Examples of the microorganisms having TCE degrading ability are limited, and they include *Welchia alkenophila* sero 5 (U.S. Pat. No. 4,877,736, ATCC53570), *Welchia alkenophila* sero 33 (U.S. Pat. No. 4,877,736, ATCC53571), *Methylosinus trichosprium* OB3b [Whitenbury R. J., Gen. Microbiol, Vol. 61, pp. 205–218 (1970)], Pseudomonas sp. G4 [Nelson M. J. K. et al., Appl. Eviron. Microbiol., Aug., pp. 383–384 (1986); Folsom B. R. et al., Appl. Eviron. Microbiol., May, pp. 1279–1285 (1990); and U.S. Pat. No. 4,925,802, ATCC53617; this bacterium has first belonged to Pseudomonas cepacia but then changed to Pseudomonas sp.], Methylomonas sp. MM2 [Henry S. M. et al., Appl. Environ. Microbiol., Jan., pp. 236–244 (1991)], *Alcaligenes denitrificans* ssp. Xylosoxidsans JE75 [Ewers J. et al., Arch. Microbiol., Vol. 154, pp. 410–413 (1990)], *Alcaligenes eutrophus* JMP 134 [Harker A. R. & Kim Y. Appl. Environ. Microbiol., Apr., pp. 1179–1181 (1990)], *Pseudomonas putida* F1 [Gibson DT et al., Biochem., Vol. 7, pp. 2653–2662 (1968); Wackett L. P. & Gibson D. T., Appl. Environ. Microbiol, July, pp. 1703–1708 (1988)], *Mycobacterium vaccse* JOB5 [Beam H. W. & Perry J. J., J. Gen. Microbiol., Vol. 82, pp. 163–169 (1974); Wackett L. P. et al., Appl. Environ. Microbiol., Nov., pp. 2960–2964 (1989), ATCC29678], *Nitrosomonas europaea* [Arciero D. et al., Biochem. Biophys. Res. Comm., Vol. 159, pp. 640–643 (1989)], *Pseudomonas fluoescens* PFL12 [Vandenbergh P. A. & Kunka B. S., Appl. Environ. Microbiol., Oct., pp. 2578–2579 (1988)], *Lactobacillus fuctivorans* RE [Kunkee, Int. J. Syst. Bact., Vol. 30, pp. 313–314 (1980), J. Appl. Bact., Vol. 34, pp. 541–545 (1971)], *Lactobacillus vaginalis* sp. nov. [Embley T. M. et al., Int. J. Syst. Bacteriol., Vol. 39, pp. 368–370 (1989), ATCC49540], and *Methylosinus trichosprium* (Japanese Patent Application Nos. 2-92274 and 3-292970).

In addition, none of the presently known bacteria can meet the practical requirements for the TCE degradation method using the microorganisms and do not possess the sufficient degrading ability.

Particularly in the case the microorganisms are used in the soil, it must be considered that the treatment is carried out in a specific environment, i.e. in the soil. The microorganisms to be used are required to have a sufficient TCE degrading activity and to effectively show this activity in the soil, but in the conventionally known bacteria, these points are not sufficient.

Nowadays, the acquisition of the bacteria which can meet practically necessary characteristics is strongly desired.

Such microorganisms are those which preferably have sufficient TCE degrading ability, are different from known bacteria in growth conditions and the like, can be applied to a wide range, are rich in utilizable morphology, and particularly can be effectively utilized in the specific environment of the soil. Examples of such additional requirements include drug resistance and an ability to utilize sucrose.

For example, in the case that the waste water containing TCE is treated, it is required that the microorganisms to be used have a TCE degrading ability, are scarcely damaged in the waste water, and can grow in the severe environment of the waste water. That is, the microorganisms having resistance to many antibiotics and assimilability to various saccharoses can probably successfully grow even in the severe environment.

Thus, the bacteria having the TCE degrading ability and more practically advantageous characteristics than the conventionally known bacteria are strongly required.

Furthermore, in biodegrading chlorinated organic compounds such as TCE, tetrachloroethylene (PCE) and dichloroethylene (DCE) in an environment of a polluted site such as a polluted soil, i.e., an open system, the density of the administered microorganisms by which the biodegradation can be carried out is noticeably decreased owing to predation by protozoans and under the influence of other native bacteria. For this reason, it is often very difficult to increase the density of the microorganisms in compliance with a required treatment ability. In order to increase the density of the microorganisms, there are a method which comprises feeding air to the soil, and a method which comprises forwarding a nutritious solution under pressure. However, although requiring a great deal of energy, these methods cannot effectively increase the number of the bacteria per unit area, and so the treatment ability of these methods remains at a low level on the whole.

In the treatment in a reactor or the like, i.e., in the treatment in a closed system, a good deal of energy for nutrient feed and aeration is also required so as to maintain the density of the microorganisms, as in the above-mentioned open system.

The microorganisms which can degrade the chlorinated organic compounds express an enzyme capable of degrading these compounds, but in order to express this kind of enzyme, an inducer is necessary.

In this case, when a large amount of the inducer is used, the degradation activity of the microorganisms increases, and this fact is known only in an example of tryptophan (WO 90/06901). However, detailed reports regrading the amount of the inducer to be used have not been present at all.

SUMMARY OF THE INVENTION

An object of the present invention is to provide a novel strain to decompose trichloroethylene and phenolic compound.

An object of the present invention is to provide a method for degrading TCE by the utilization of microorganisms.

Another object of the present invention is to provide a method for remediating a soil by the utilization of microorganisms.

Still another object of the present invention is to provide a method for obtaining microorganisms useful for the degradation of TCE.

A further object of the present invention is to provide a method for biodegrading chlorinated organic compounds by heightening degradation activity per unit weight of microorganisms capable of degrading the chlorinated organic compounds, whereby a sufficient degrading treatment ability can be obtained even in an open system such as a soil in which an increase in the number of bacteria cannot be expected.

A still further object of the present invention is to provide a method for biodegrading chlorinated organic compounds by which a satisfactory degradation treatment ability can be obtained even in a closed system and even by a small number of bacteria to permit decreasing energy and cost required for the increase and the maintenance of the number of bacteria.

A still further object of the present invention is to provide a practical method of decomposing a phenolic compound using microorganisms.

A still further object of the present invention is to provide a practical method of biologically decomposing a furan compound using appropriate microorganisms.

A still further object of the present invention is to provide a method of obtaining microorganisms useful for decomposing a furan compound.

A further object of the present invention is to provide a practical method of producing 2-furan carboxylic acid using appropriate microorganisms.

These objects can be accomplished by the following present invention.

That is, the first aspect of the present invention is directed to a method for biodegrading trichloroethylene which comprises the step of bringing an aqueous medium containing trichloroethylene into contact with microorganisms having a trichloroethylene degrading ability derived from intestines of termites to degrade trichloroethylene.

The second aspect of the present invention is directed to a method for obtaining microorganisms having a trichloroethylene degrading ability which comprises the steps of culturing microorganisms separated from the bodies of termites in a culture medium.

The third aspect of the present invention is directed to a method for remediating a soil which comprises the step of bringing trichloroethylene in the soil into contact with microorganisms having a trichloroethylene degrading ability derived from intestines of termites to degrade trichloroethylene.

The fourth aspect of the present invention is directed to a biodegradation method for degrading a chlorinated organic compound by bringing microorganisms, whose degrading activity can be induced with an inducer, into contact with the chlorinated organic compound in the presence of the inducer to degrade the chlorinated organic compound, the amount of the inducer being such as to meet the following relation:

$$2\int_0^T f(t)dt - T \cdot f(T) \geq 0$$

(wherein T is a culture time when the bacterial number y is maximum), when the microorganisms are cultured by a batch system in the presence of the inducer and the growth curve of the microorganisms is close to y=f(t) (wherein y is a bacteria number determined by an optical density (O.D.), and t is a culture time).

The fifth aspect of the present invention is directed to a method of biologically decomposing a phenolic compound comprising the step of decomposing a phenolic compound by bringing an aqueous solution containing the phenolic compound into contact with the intestinal microorganisms of termites.

The sixth aspect of the present invention is directed to a method of obtaining microorganisms having the ability to decompose a phenolic compound comprising the steps of culturing the microorganisms isolated from the intestines of termites in a medium containing a phenolic compound as a single carbon source and recovering the grown microorganisms.

The seventh aspect of the present invention is directed to method of biologically decomposing a furan compound comprising the step of decomposing a furan compound in the presence of the intestinal microorganisms of termites having the ability to decompose the furan compound.

The eighth aspect of the present invention is directed to a method of obtaining microorganisms having the ability to decompose a furan compound comprising the steps of culturing the microorganisms isolated from the intestines of termites in a medium containing a furan compound as a single carbon source, and recovering the grown microorganisms.

The ninth aspect of the present invention is directed to a strain of *Pseudomonas cepacia* derived from the intestines of termites and having the ability to decompose a phenolic compound or a furan compound.

The tenth aspect of the present invention is directed to a strain of *Pseudomonas cepacia* KK01 (FERM BP4235) derived from the intestine of a termite and having the ability to decompose a phenolic compound or a furan compound.

The eleventh aspect of the present invention is directed to a method of producing 2-furan carboxylic acid comprising the step of oxidizing furfural by means of the intestinal microorganisms of termites to obtain 2-furan carboxylic acid.

DESCRIPTION OF THE PREFERRED EMBODIMENTS

Figure 1:
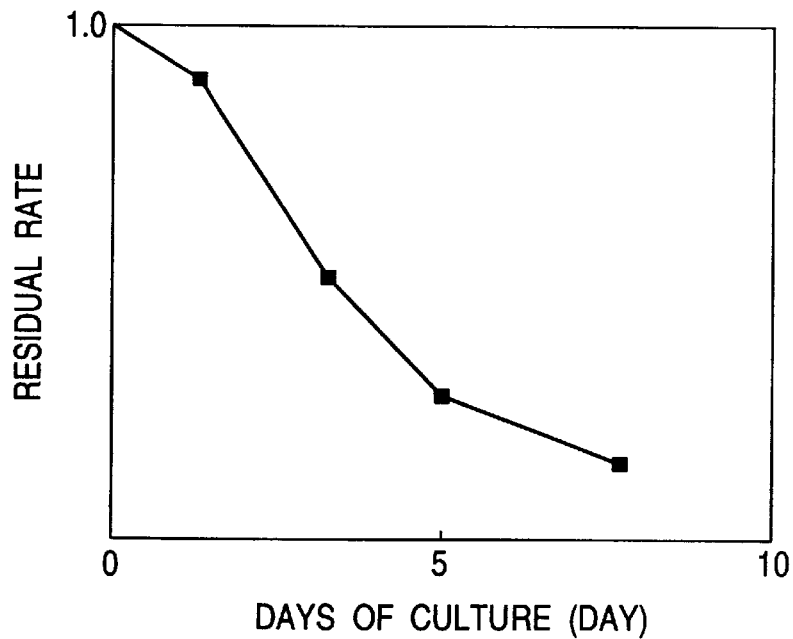
FIG. 1 is a graph showing daily changes of the residual rate of phenol in a culture medium measured in Example 1.

The microorganisms used in a decomposition method of the present invention and derived from the intestines of termites can be obtained by, for example, washing the surfaces of termites so as to sterilize the surface extracting the intestines and grinding them in an appropriate solution, adding a part of the resulting mixture containing the ground intestines to a culture medium containing as a single carbon source a phenolic compound or a furan compound to be decomposed, and isolating the grown strain. Although various kinds of termites can be used, termites belonging to the genuses Nasutiterminae such as *Nasutitermes takasagoensis, Nasutitermes ephratae, Nasutitermes exitiosus, Nasutitermes nigriceps* and the like are preferable. *Nasutitermes takasagoensis* is particularly preferable.

A medium containing as a single carbon source a phenolic compound or a furan compound, and if required, various nitrogen sources, inorganic salts, growth factors and the like, can be used as a medium for screening microorganisms having the ability to decompose the phenolic compound or furan compound. For example, in the case of the bacteria belonging to Pseudomonas, yeast extract and peptone can be used singly or in combination thereof as a nitrogen source, and potassium hydrogen primary phosphate, ammonium chloride or the like can be used as an inorganic salt. The concentration of the phenolic compound can be appropriately selected, for example, to be set in the range of 0.02 to 0.07%. The concentration of the furan compound can be appropriately selected, for example, to be set in the range of 0.01 to 0.05%.

The thus-isolated microorganisms can be cultured under conditions appropriately selected which are suitable for the microorganisms.

The phenolic compound or furan compound can be decomposed by using the isolated microorganisms. A mixture of at least two microorganisms having the ability to decompose the phenolic compound or furan compound may be used for decomposing the compound. When a mixture is used, a mixture having a known microorganism composition or having an unknown composition and exhibiting the ability to decompose the phenolic compound or furan compound can be used. Even when the screening medium contains various kinds of microorganisms, the medium can be used as a mixture system without isolation of the respective microorganisms. The *Pseudomonas cepacia* KK01 strain or the like can be used as an isolated strain. A mutant obtained by naturally or artificially modifying the intestinal microorganisms of termites and having the ability to decompose the phenolic compound or the furan compound can also be used in the present invention.

The KK01 strain has resistance to various kinds of antibiotics, and permits various kinds of sugar to be utilized as a carbon source, as described in the examples below. The strain also has the ability to decompose phenol, the ability to decompose cresol and the ability to decompose tetrahydrofuran, furfuryl alcohol and cumaran. The KK01 strain is thus practically useful for biologically decomposing phenolic and furan compounds.

In the present invention, a phenolic compound or a furan compound contained in a substance such as waste water to be treated can be decomposed by bringing the phenolic compound or furan compound into contact with the intestinal microorganisms of termites. The contact between the microorganisms and the substance to be treated can be performed by a method of culturing the microorganisms in an aqueous solution containing the phenolic compound or furan compound to be decomposed, or by a method of adding the aqueous solution to a culture system of the microorganisms. The methods can be performed in one of various systems such as a batch system, a semi-continuous system, a continuous system and the like. The microorganisms can be used in an unbound state or state wherein they are bound to an appropriate carrier. The substance such as waste water to be treated may be subjected to various pretreatments as needed. For example, pretreatment may be performed for controlling the concentration of the phenolic compound or the furan compound and the pH of the liquid, or supplying various nutritive substances such as the yeast extract and the like. The concentration of the phenolic compound within the decomposition region may be adjusted to about 0.2% or less in the presence of other nutritive substances such as yeast extract and the like. For example, the concentration of the furan compound within the decomposition region may be adjusted to about 0.05% in the presence of other nutritive substances such as the yeast extract and the like.

The 2-furan carboxylic acid producing method of the present invention comprises the step of obtaining 2-furan carboxylic acid from furfural or furfuryl alcohol by means of the intestinal microorganism of termites.

The microorganisms used for producing 2-furan carboxylic acid can be obtained by selecting microorganisms which produce 2-furan carboxylic acid from the microorganisms obtained by the screening and having the ability to decompose furfural or furfuryl alcohol.

In the present invention, 2-fural carboxylic acid can be produced by bringing furfural into contact with the intestinal microorganisms of termites. The contact of a raw material compound with the microorganisms can be performed by a method of culturing the microorganisms in an aqueous solution containing the raw material compound, or a method of adding the aqueous solution to a culture system of the microorganisms. These methods can be performed in one of various systems such as a batch system, a semi-continuous system, a continuous system and the like. The microorganisms can be used in an unbound state or a state wherein they are bound to an appropriate carrier. The concentration of the raw material compound, i.e, furfural, pH, and the concentrations of various nutritive substances can be appropriately selected in accordance with the microorganisms used. For example, the concentration of the raw material compound may be adjusted to about 0.05% in the presence of other nutritive substances such as yeast extract. The culture is preferably performed under aerobic conditions at about 30° C. When waste water containing the raw material compound is used, pretreatment may be made for adjusting the concentration of the raw material compound and the pH of the liquid, or supplying various nutritive substances.

A method for biodegrading TCE of the present invention is characterized by comprising the step of bringing an aqueous medium containing trichloroethylene into contact with microorganisms derived from intestines of termites which have an ability to degrade trichloroethylene, thereby degrading trichloroethylene.

Furthermore, a method for remediating a soil is characterized by comprising the step of bringing, in the soil, trichloroethylene into contact with microorganisms derived from intestines of termites which have an ability to degrade trichloroethylene, thereby degrading trichloroethylene to remediate the soil.

The microorganisms derived from the intestines of termites which can be used in the method of the present invention can be obtained by, for example, sterilizably washing the surfaces of the termites, taking intestines out of the termites and crushing them in a suitable solution, and isolating a strain from a part of the mixture containing the crushed intestines, this strain being screened on the basis of the TCE degrading ability. In the present invention, the various kinds of termites can be used, but preferable examples of the termites include *Nasutitermes takasaqoensis, Nasutitermes ephratae, Nasutitermes exitiosus. Nasutitermes nigriceps* in a Nasutiterminae genus. Above all, *Nasutitermes takasagoensis* is particularly preferable.

As a culture medium for screening the microorganisms having the TCE degrading ability, there can be utilized a culture medium containing TCE, and if necessary a carbon source, a nitrogen source, an inorganic salt and a growing factor. For example, in the case of Pseudomonas bacteria, yeast extract and peptone can be used singly or in combination as the nitrogen source, and potassium primary hydrogenphosphate, ammonium chloride or the like can be utilized as the inorganic salt. The concentration of TCE can be suitably selected. Cultivation can be carried out under conditions in compliance with the kind of microorganisms to be separated. In the case that the microorganisms which cannot be grown only by TCE are separated, an isolated strain is cultured in a culture medium containing the carbon source, for example phenol and the like, necessary to grow, and the microorganisms having the TCE degrading ability can be then selected.

The thus separated microorganisms can be used to carry out the degradation treatment of TCE. In the degradation treatment, one kind or a mixed system of two or more kinds of microorganisms having the TCE degrading ability can be used. In the case where the mixed system is used, the microorganisms whose composition is known or unknown but which have the TCE degrading ability can be utilized. Therefore, even when a plurality of kinds of microorganisms are contained in the culture medium for the above-mentioned screening, these microorganisms can be utilized as the mixed system without separation. As the isolated strain, a *Ps. cenacia* strain KK01 or the like can be utilized. Additionally, in the present invention, there can also be used a variant obtained by naturally or artificially varying the microorganisms having the TCE degrading ability separated from intestines of the termites.

The strain KK01 is characterized by growing in the presence of a phenolic compound alone, degrading the phenolic compound, having resistance to antibiotics, utilizing various kinds of saccharoses as shown in the undermentioned examples, and having the TCE degrading ability.

In the present invention, the degradation treatment of TCE can be carried out by bringing TCE in a material to be treated such as waste water into contact with the above-mentioned microorganisms derived from the intestines of the termites. This contact of the microorganisms with the material to be treated is achieved by culturing the microorganisms in the aqueous liquid containing TCE to be degraded, or adding the aqueous liquid to the culture medium of the microorganisms. In this case, an optional process such as a batch process, a semi-continuous process or a continuous process can be used. The microorganisms, when used, may not be fixed or may be fixed on a suitable carrier. The material to be treated such as waste water may be subjected to a suitable pretreatment, if necessary. For example, the adjustment of a TCE concentration or a pH, or the supplementation of various nutrients may be carried out. In the degradation range, the TCE concentration is preferably adjusted to about 100 ppm or less in the presence of another nutrient such as yeast extract.

The method for remediating a soil of the present invention can be carried out by bringing the microorganisms having the TCE degrading ability into contact with TCE in the soil. The contact of the microorganisms with the soil can be achieved by directly introducing the microorganisms into the soil, supporting the microorganisms on a carrier and then introducing the carrier into the soil, or the like. The amount of the microorganisms to be fed to the soil depends upon growing factors of the microorganisms in the soil such as a pollution degree of the soil, a nutritious state, temperature and oxygen concentration.

The present inventors have paid attention to and investigated the amount of an inducer to be added at the time of the degradation with the intention of heightening the degradation activity of the microorganisms capable of degrading the chlorinated organic compounds. As a result, they have found that there is correlation between the amount of the inducer which can heighten the degradation activity and the shape of a bacteria growth curve at an early stage of the batch culture of the microorganisms in the presence of the inducer, i.e., the growth characteristics of the microorganisms. That is, it has been found that in order to heighten the degradation activity, the amount of the inducer must be in the range in which the above-mentioned growth curve meets the following relation $$2\int_0^T f(t)dt - T \cdot f(T) \geq 0$$

(wherein T is a culture time when the bacterial number y is maximum), when the microorganisms are cultured by a batch system in the presence of the inducer and the growth curve of the microorganisms is close to y=f(t) (wherein y is a bacteria number determined by an optical density (O.D.), and t is a culture time).

In consequence, the present invention has now been achieved.

The reason why the above-mentioned relation is established cannot be definitely elucidated at present, but this relation has been confirmed with regard to many kinds of microorganisms under many conditions. Furthermore, it has been confirmed that the above-mentioned relation can be applied to a closed batch reactor, an open continuous reactor and a complex heterogeneous system such as a soil.

No particular restriction is put on the microorganisms which can be used in the method of the present invention, so long as they can induce the degradation activity to the chlorinated organic compounds with the aid of the inducer and also have the degradation activity to the inducer. As such microorganisms, there can be utilized unidentified microorganisms, mixed microorganisms which are not isolated, symbiotic microorganisms, and isolated and identified microorganisms. Examples of the identified microorganisms include bacteria belonging to a Pseudomonas genus, an Acinetobactor genus, a Methylocystis genus and a Methylosinus genus, and among them, the bacteria having the above-mentioned characteristics can be used in the present invention. Examples of the usable microorganisms include *Methylosinus trichosporium* OB3b capable of degrading TCE in the presence of methane, and a Pseudomonas cepacia strain KK01 which requires phenol as the inducer.

The chlorinated organic compounds to be degraded include ethylene chlorides such as TCE and DCE.

The inducer can be selected in compliance with the kind of microorganisms to be used, and examples of the inducer include methane, and aromatic compounds such as phenol, toluene and cresol.

The method of the present invention can be applied to either of a closed system and an open system such as a waste water treatment and a soil treatment. In addition, the microorganisms may be supposed on a carrier, or an optional technique for accelerating the growth may be employed.

EXAMPLES

The present invention is described in further detail below with reference to examples. The M9 medium used in each of the examples has the following composition:

M9 medium composition (per liter)

| | |
|---|---|
| $NaHPO_4$ | 6.2 g |
| $KH_2PO_4$ | 3.0 g |
| NaCl | 0.5 g |
| $NH_4Cl$ | 1.0 g |
| (pH 7.0) | |

Example 1

(Screening by phenol)

Ten worker termites *Nasutitermes takasagoensis* were placed on a plate, and ethyl alcohol (95%) was poured into the plate so as to sterilize the surfaces of the termites. The ethyl alcohol was removed by washing the termites twice in the M9 medium containing 0.05% phenol. After washing, the intestine was picked out from each termite with a pair of tweezers, and was then ground in the M9 medium containing 0.05% phenol to obtain a liquid mixture containing the ground intestines. A portion of the resulting mixture was inoculated into the M9 medium containing 0.05% phenol and 0.05 t yeast extract, followed by culture under aerobic conditions at 30° C. The daily change in the amount of phenol contained in the medium was measured. The amount of the phenol contained in the medium was measured by the method below. The medium was sampled, and the sample obtained was passed through a filter of 0.2 μm. The concentration of phenol in the filtrate obtained was determined by measuring light absorption at about 270 nm using a spectrophotometer. The phenol concentration was indicated by a residual rate of phenol. The results obtained are shown in FIG. 1. The results shown in FIG. 1 reveals that microorganisms which assimilate phenol are present in the intestine of a termite.

Example 2

(Screening by o-cresol)

Figure 2:
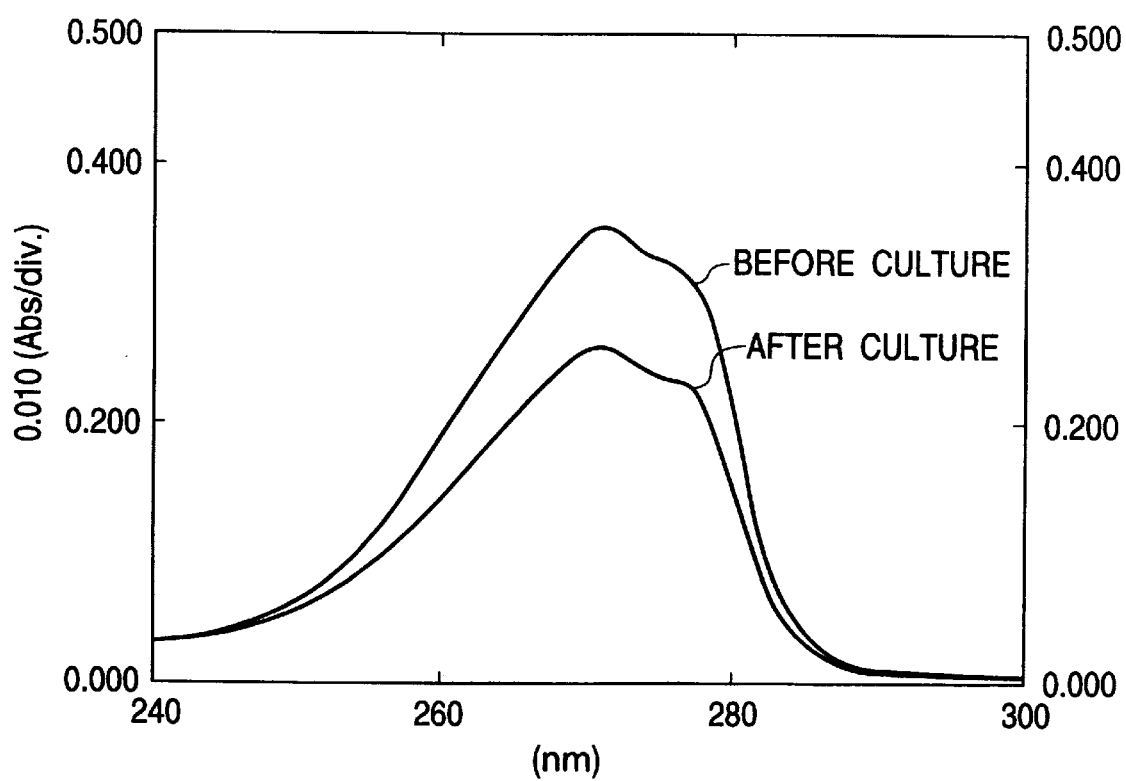
FIG. 2 is a graph showing a difference in the ultraviolet absorption spectra of a culture solution measured before and after culture in Example 2.

Ten worker termites *Nasutitermes takasaqoensis* were placed on a plate, and ethyl alcohol (95%) was poured into the plate so as to sterilize the surfaces of the termites. The ethyl alcohol was removed by washing the termites twice in the M9 medium containing 0.02% o-cresol. After washing, the intestine was picked out from each termite with a pair of tweezers, and was then ground in the M9 medium containing 0.02% o-cresol to obtain a liquid mixture containing the ground intestines. A portion of the resulting mixture was inoculated into the M9 medium containing 0.02% o-cresol and 0.05% yeast extract, followed by culture under aerobic conditions at 30° C. for 10 days. A difference in the amounts of o-cresol contained in the M9 medium before and after culture was determined by measuring the ultraviolet absorption spectrum of the medium before the inoculation and after culture. After culture, the medium was passed through a filter of 0.22 μm, and the ultraviolet absorption spectrum of the filtrate obtained was then measured. The results obtained are shown in FIG. 2. The results shown in FIG. 2 reveals that microorganisms which assimilate a phenolic compound such as o-cresol are present in the intestine of a termite.

Example 3

(Screening by m-cresol)

Figure 3:
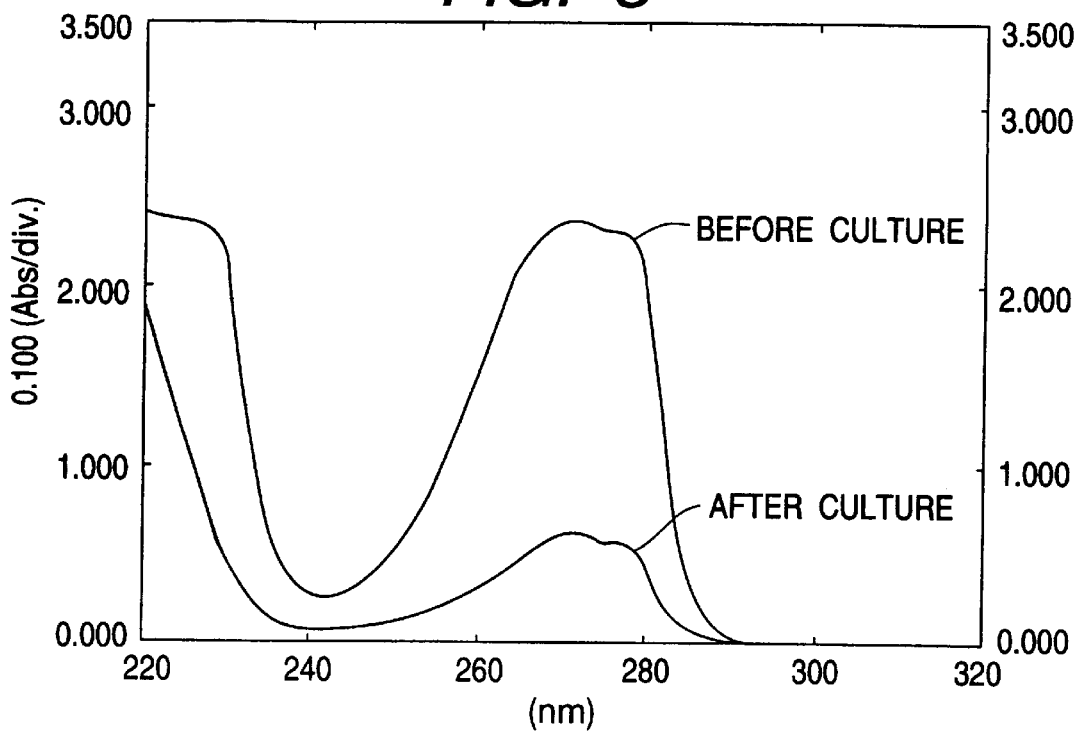
FIG. 3 is a graph showing a difference in the ultraviolet absorption spectra of a culture solution measured before and after culture in Example 3.
Figure 4:
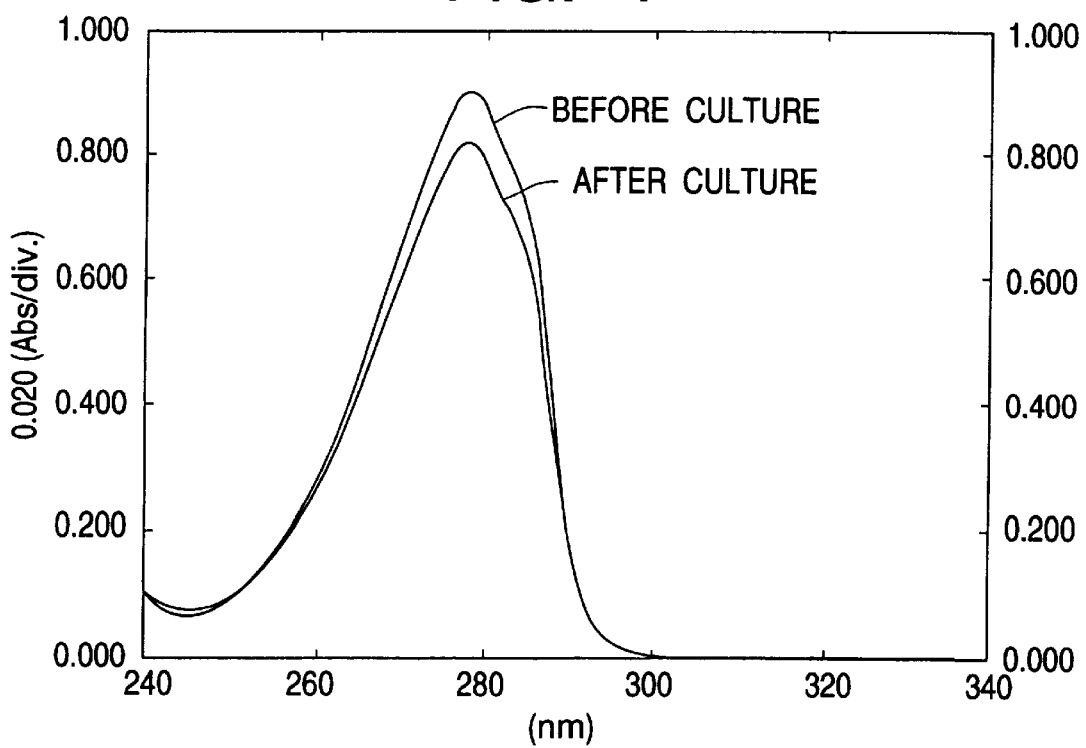
FIG. 4 is a graph showing a difference in the ultraviolet absorption spectra of a culture solution measured before and after culture in Example 4.

The same operation as that performed in Example 2 were performed except that m-cresol was used in place of o-cresol. As shown in FIG. 3, a reduction in the amount of m-cresol contained in the medium was apparent. This indicates that microorganisms which assimilate m-cresol are present in the intestine of a termite.

Example 4

(Screening by p-cresol)

The same operation as that performed in Example 2 were performed except that p-cresol was used in place of o-cresol. As shown in FIG. 3, a reduction in the amount of p-cresol contained in the medium was indicated. This shows that microorganisms which assimilate p-cresol are present in the intestine of a termite.

Example 5

(Acquisition of isolated strain using phenol)

The medium (containing grown bacteria) obtained by culturing the M9 medium (containing 0.05 t phenol and 0.05% yeast extract) used in Example 1 was coated on the surface of a phenol-containing M9 agar medium (containing 0.05% phenol and 1.2% agar), followed by culture under aerobic conditions at 30° C. for 2 days. The colonies which grew well on the agar medium were collected to obtain an isolated strain. As a result of examination of the mycological characters of a portion of the isolated strains, the results shown below were obtained. It was concluded that the isolated strain is *Pseudomonas cepacia*.

A. Morphological character (1) Gram's strain: negative (2) Size and form of strain: bacillus having a length of 1.0 to 2.0 μm and a width of about 0.5 μm (3) Mobility: present B. Growth states in various media

TABLE 1

| Medium | Culture Temperature (° C.) | Growth state |
|---|---|---|
| Blood agar | 37 | + |
| Lactose agar | 37 | + |
| Chocolate agar | 37 | ++ |
| GMA | 37 | − |
| Scyllo | 37 | − |
| Nutrient agar | 4 | − |
| Nutrient agar | 25 | ± |
| Nutrient agar | 37 | + |
| Nutrient agar | 41 | ± |

C. Physiological character (1) Distinction between aerobic and anaerobic: obligate aerobic
(2) Decomposition type of sugar: oxidative
(3) Generation of oxidase: +
(4) Reduction of silver nitrate: +
(5) Generation of hydrogen sulfide: −
(6) Generation of indole: −
(7) Generation of urease: −
(8) Liquefaction of gelatin: −
(9) Hydrolysis of arginine: −
(10) Decarboxylation of lysine: +
(11) Decarboxylation of ornithine:
(12) Utilization of citric acid: +
(13) Methylcarbinol acetyl reaction (VP reaction): −
(14) Detection of tryptophan deaminase: −
(15) ONPG: −
(16) Utilization of carbohydrates:
  Grape sugar: +
  Fractose: +
  Maltose: +
  Galactose: +
  Xylose: +
  Mannitol: +
  Saccharose: −
  Lactose: +
  Escurin: −
  Inositol: −
  Sorbitol: −
  Rhamnose: −
  Melibiose: −
  Amygdalin: −
  L-(+)-arabinose: +

This strain was cultured in the M9 medium (5 ml) containing 0.05% phenol and 0.05% yeast extract at 30° C. After a predetermined number of days have passed, the bacteria were separated from the medium by passing the medium through a filter of 0.22 μm. The concentration of phenol of the filtrate obtained was determined by measuring light absorption at about 270 nm using a spectrophotometer. The daily changes in the rate of removal (residual rate) of phenol from the medium were measured in the same way as that in Example 1. The results obtained are shown in FIG. 5.

Figure 5:
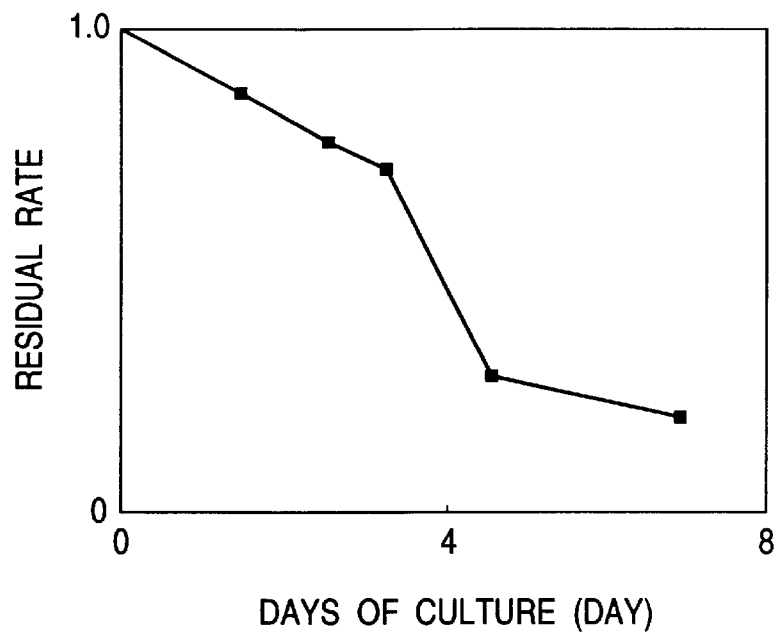
FIG. 5 is a graph showing daily changes of the residual rate of phenol in a culture medium measured in Example 5.

As is obvious from the results shown in FIG. 5, the strain has excellent ability to decompose phenol. Since strains having the ability to decompose phenol are not found in the generally known strains of *Pseudomonas cepacia,* it was recognized that the strain is a new strain. The strain was named KK01 strain and deposited in Fermentation Research Institute of the Agency of Industrial Science and Technology Ibaraki, Japan (Deposition Date: Mar. 11, 1992; Deposition No. FERM BP-4235).

Example 6

(Acquisition of isolated strain using o-cresol)

The medium (containing grown bacteria) obtained by culture in the M9 medium containing 0.02% o-cresol and 0.05% yeast extract in Example 2 was coated on the surface of a o-cresol-containing M9 agar medium (containing 0.02% o-cresol and 1.2% agar), followed by culture under as aerobic conditions at 30° C. for 5 days. The colonies which grew well on the agar medium were collected as an isolated strain. Examination of the mycological characters of a portion of the strain showed the same results as those of the KK01 strain obtained in Example 5. The isolated strain was identified as the KK01 strain.

Example 7

(Acquisition of isolated strain using m-cresol)

The medium (containing grown bacteria) obtained by culture in the M9 medium containing 0.02% m-cresol and 0.05% yeast extract in Example 3 was coated on the surface of a m-cresol-containing M9 agar medium (containing 0.02% m-cresol and 1.2% agar), followed by culture under aerobic conditions at 30° C. for 5 days. The colonies grown well on the agar medium were collected to obtain an isolated strain. Examination of the mycological characters of a portion of the strain showed the same results as those of the KK01 strain obtained in Example 5. The isolated strain was thus identified as the KK01 strain.

Example 8

(Acquisition of isolated strain using p-cresol)

The medium (containing grown bacteria) obtained by culture in the M9 medium containing 0.02% p-cresol and 0.05% yeast extract in Example 4 was coated on the surface of a p-cresol-containing M9 agar medium (containing 0.02% p-cresol and 1.2% agar), followed by culture under aerobic conditions at 30° C. for 5 days. The colonies grown well on the agar medium were collected to obtain an isolated strain. Examination of the mycological characters or a portion of the strain showed the same results as those of the KK01 strain obtained in Example 5. The isolated strain was thus identified as the KK01 strain.

Example 9

(Measurement of removal rate of cresol)

Figure 6:
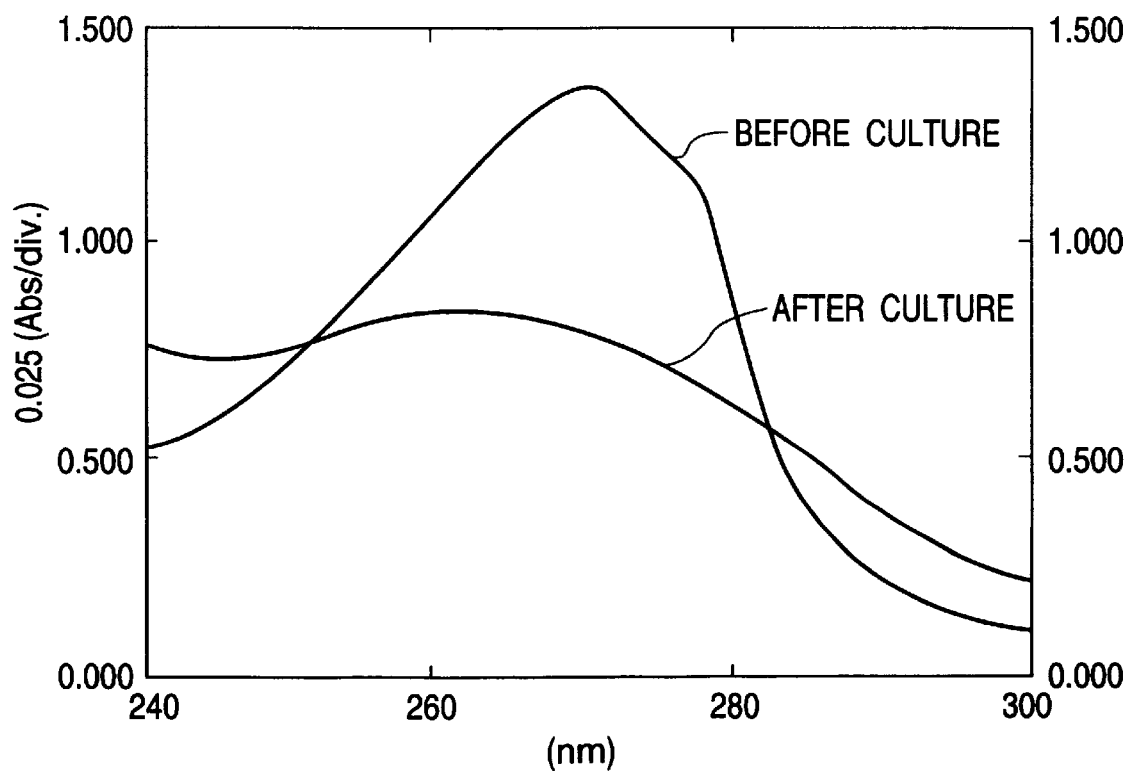
FIG. 6 is a graph showing a difference in the ultraviolet absorption spectra of a culture solution measured before and after culture in Example 9.

The KK01 strain obtained in Example 6 was cultured in a M9 medium (5 ml) containing 0.02% o-cresol and 0.05% yeast extract at 30° C. for 7 days. A difference (removal rate) in the amounts of o-cresol contained in the medium before and after culture was determined by measuring the ultraviolet absorption spectrum of the medium before inoculation and after culture. In order to perform the measurement, the medium was passed through a filter of 0.22 μm after culture, and the ultraviolet absorption spectrum of the filtrate obtained was measured. The results obtained are shown in FIG. 6.

Figure 7:
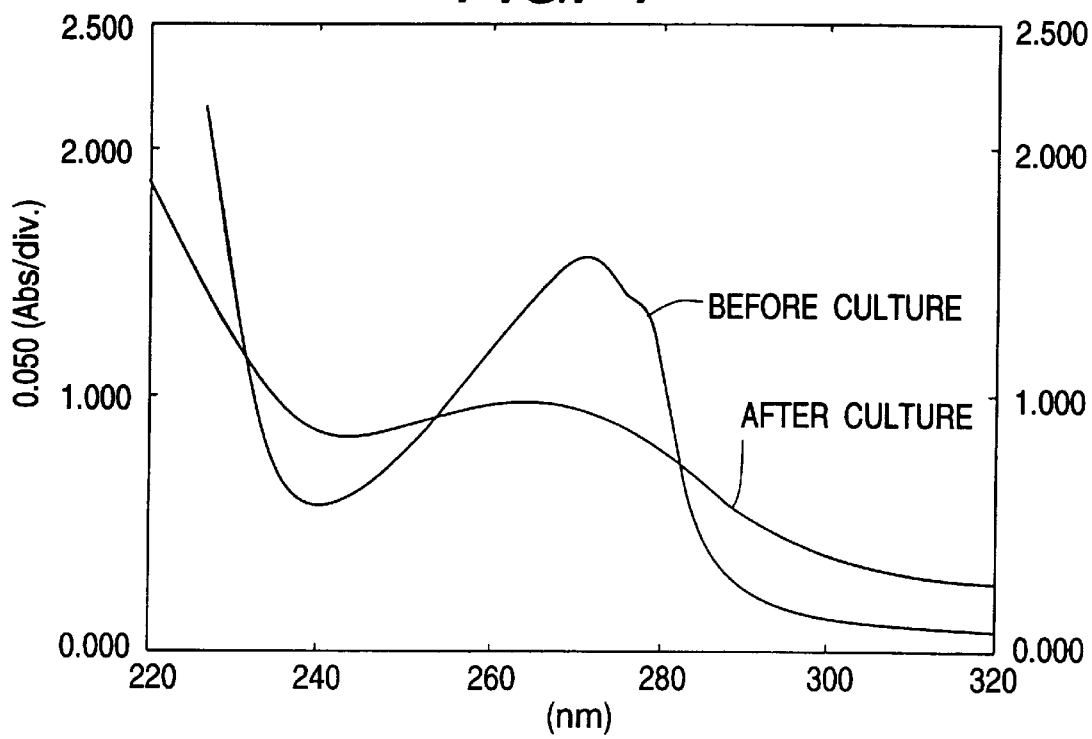
FIG. 7 is a graph showing a difference in the ultraviolet absorption spectra of a culture solution measured before and after culture in Example 9.
Figure 8:
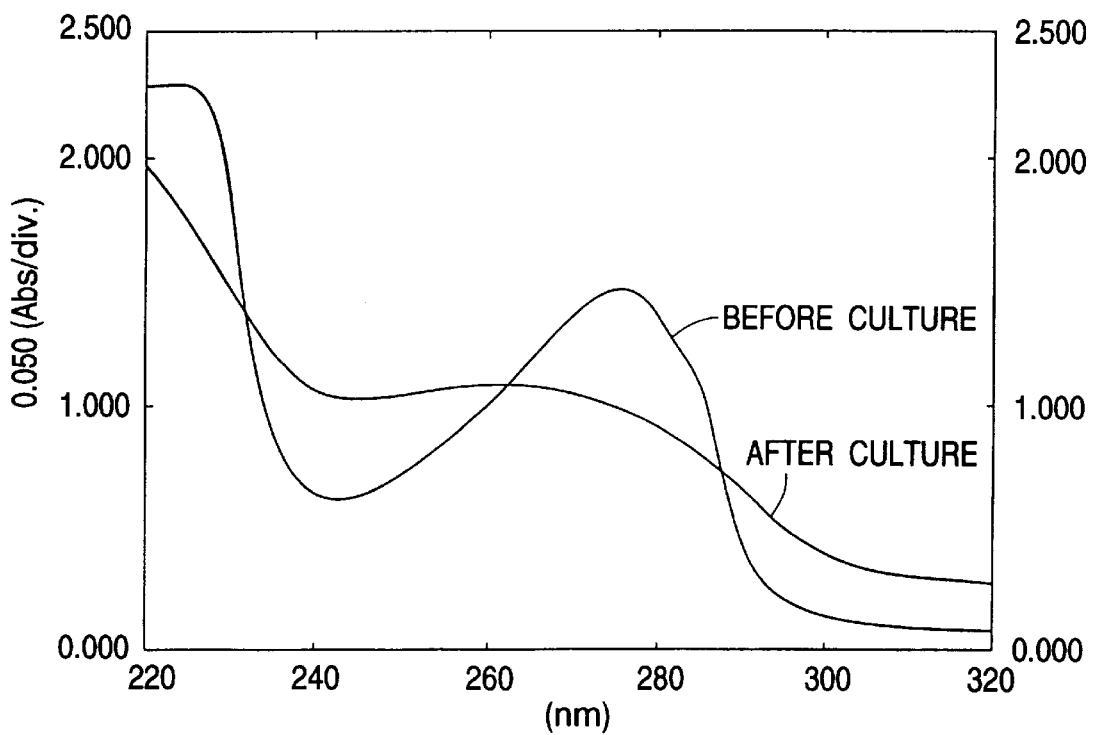
FIG. 8 is a graph showing a difference in the ultraviolet absorption spectra of a culture solution measured before and after culture in Example 9.

The removal rates of m-cresol and p-cresol were measured by the same method as that described above except that o-cresol was replaced by m-cresol and p-cresol, respectively. The results obtained are shown in FIGS. 7 and 8. As is obvious from the results shown in FIGS. 6 to 8, the strain of the present invention has not only the ability to decompose phenol but also the ability to decompose cresol. This property is not exhibited by generally known strains of *Pseudomonas cepacia*.

Example 10

The KK01 strain was inoculated into the synthetic waste water artificially formed having the composition below, and was cultured under aerobic conditions at 30° C. The changes with time of the amount of phenol contained in the medium were determined by measuring the ultraviolet absorption spectrum of the medium in the same manner as that employed in each of the examples.

Synthetic waste water composition:

| | |
|---|---|
| Phenol | 200 mg |
| o-cresol | 50 mg |
| m-cresol | 40 mg |
| p-cresol | 50 mg |
| $NH_4Cl$ | 200 mg |
| $KH_2PO_4$ | 272 mg |
| $Na_2HPO_4$ | 284 mg |
| Water | 1 l |
| pH (7.0) | |

Figure 9:
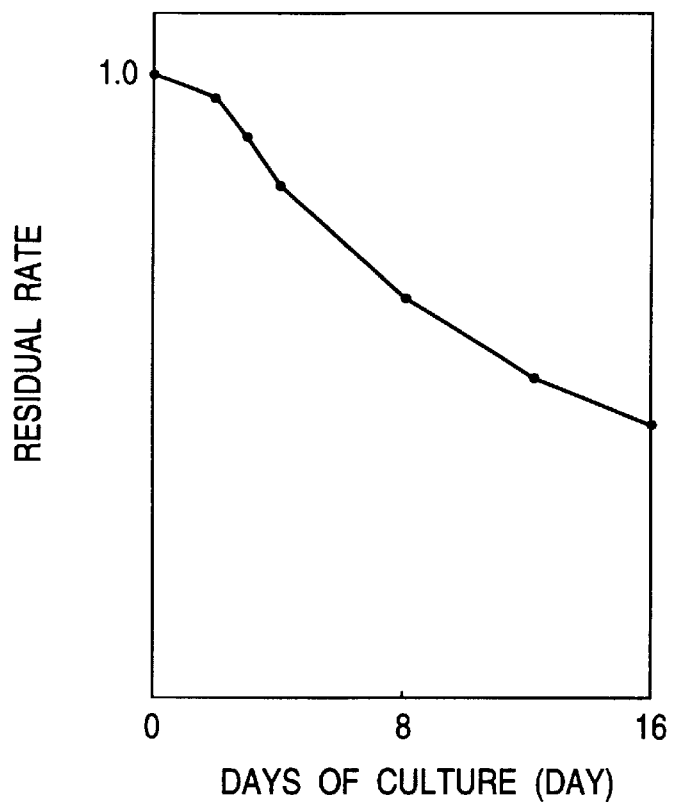
FIG. 9 is a graph showing daily changes in the residual rate of a phenolic compound in a waste liquid measured in Example 10.

The results obtained are shown in FIG. 9. It was determined from the results that the KK01 strain has the ability to decompose the phenol and cresol contained in the synthetic waste water.

Example 11

(Screening by furfural)

Figure 10:
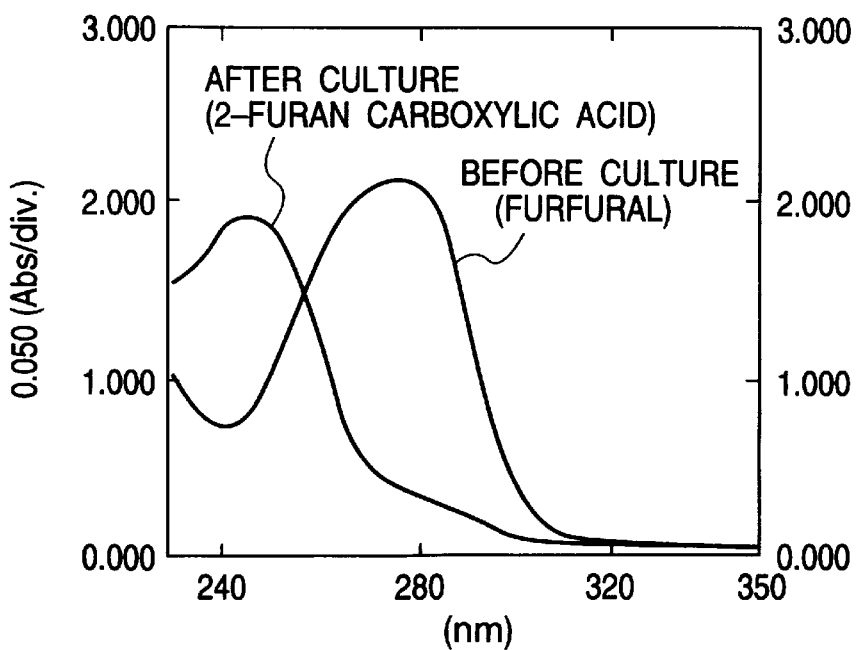
FIG. 10 is a graph showing a difference in the ultraviolet absorption spectra of a culture solution measured before and after culture in Example 11.

Ten worker termites *Nasutitermes takasagoensis* were placed on a plate, and ethyl alcohol (95%) was poured into the plate so as to sterilize the surfaces of the termites. The ethyl alcohol was removed by washing the termites twice in the M9 medium containing 0.02% furfural. After washing, the intestine was picked out from each termite with a pair of tweezers, and was then ground in the M9 medium containing 0.02% furfural to obtain a liquid mixture containing the ground intestines. A part of the resulting mixture was inoculated into the M9 medium containing 0.02% furfural and 0.05% yeast extract, followed by culture under aerobic conditions at 30° C. for 15 days. The absorbance (230 to 350 nm) of the medium was measured before and after culture by a spectrophotometer. In order to perform the measurement, the medium was filtered through a filter of 0.22 μm for removing the bacteria and the like after culture and was then measured. The results obtained are shown in FIG. 10. As shown in FIG. 10, an absorption peak at about 280 nm which indicates the presence of furfural appears in the spectrum measured before culture and disappears from the spectrum measured after culture. While a peak indicating the presence of 2-furan carboxylic acid appears at about 247 nm. The results show that furfural is converted to 2-furan carboxylic acid by culture of the isolated bacteria.

Example 12

(Acquisition of isolated strain using furfural)

The medium (containing grown bacteria) obtained by culture in the M9 medium (further containing 0.02% furfural and 0.05% yeast extract) in Example 11 was coated on the surface of a furfural-containing M9 medium (containing 0.05% furfural and 1.2% agar), followed by culture at 30° C. The colonies which grew well on the medium were collected to obtain an isolated strain. Examination of the mycological character of a portion of the isolated strain showed the same results as those of the KK01 strain obtained in Example 5. The isolated strain was thus identified as the KK01 strain.

Example 13

(Screening by tetrahydrofuran)

Figure 11:
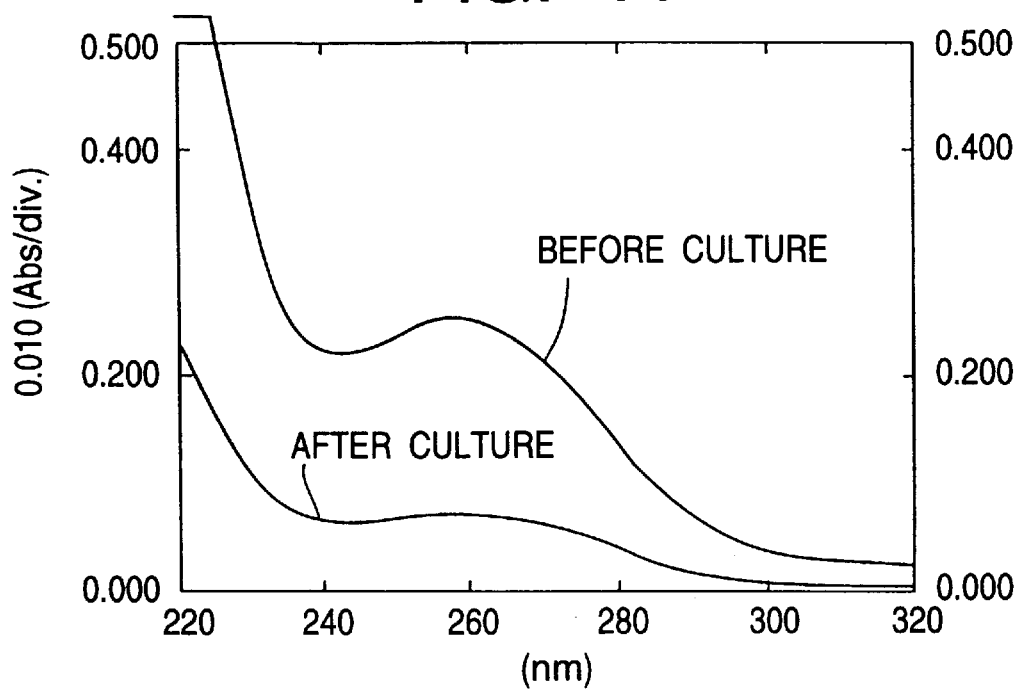
FIG. 11 is a graph showing a difference in the ultraviolet absorption spectra of a culture solution measured before and after culture in Example 13.

Microorganisms having the ability to decompose tetrahydrofuran were isolated from the intestines of termites by the same method as that employed in Example 11 except that tetrahydrofuran was used in place of furfural. The absorbance (220 to 320 nm) of the medium was measured before and after culture. The results obtained are shown in FIG. 11. It was confirmed by the results shown in FIG. 11 that microorganisms having the ability to decompose tetrahydrofuran are present in the intestine of a termite.

Example 14

(Acquisition of isolated strain using tetrahydrofuran)

The medium (containing grown bacteria) obtained by culture in the M9 medium (further containing 0.02% tetrahydrofuran and 0.05% yeast extract) in Example 13 was coated on the surface of a tetrahydrofuran-containing M9 medium (containing 0.05% tetrahydrofuran and 1.2% agar), followed by culture at 30° C. The colonies which grew well on the medium were collected to obtain an isolated strain. Examination of the mycological characters of a portion of the isolated strain showed the same results as those of the KK01 strain obtained in Example 5. The isolated strain was thus identified as the KK01 strain.

Example 15

(Screening by furfuryl alcohol)

Figure 12:
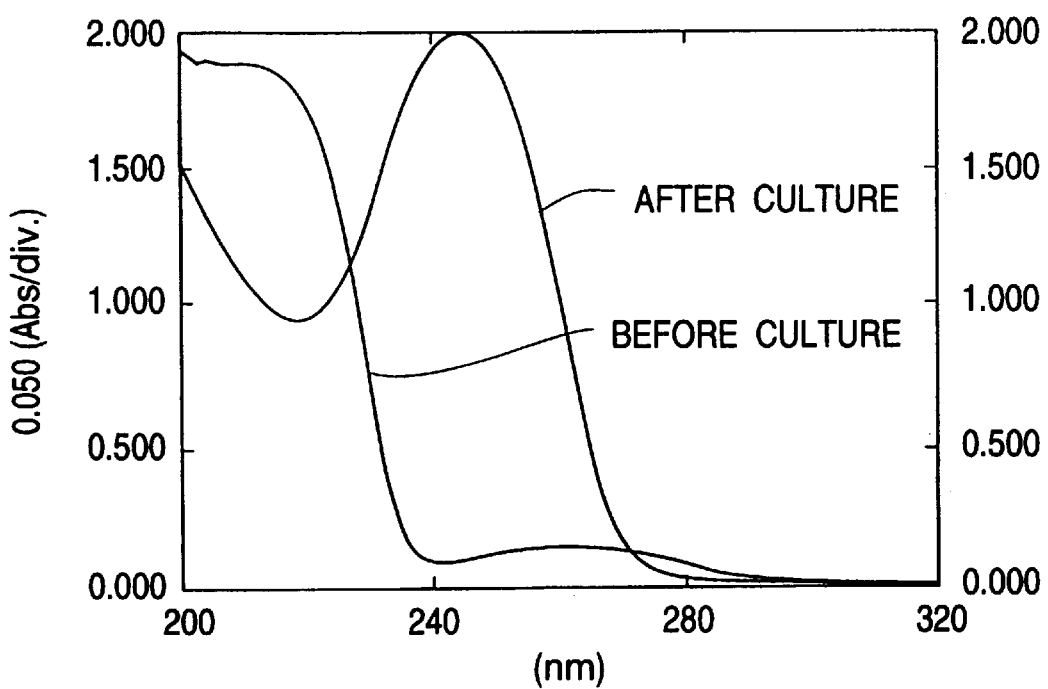
FIG. 12 is a graph showing a difference in the ultraviolet absorption spectra of a culture solution measured before and after culture in Example 15.

Microorganisms having the ability to decompose furfuryl alcohol were isolated from the intestines of termites by the same method as that employed in Example 11 except that furfuryl alcohol was used in place of furfural. The absorbance (220 to 320 nm) of the medium was measured before and after culture. The results obtained are shown in FIG. 12. It was confirmed by the results shown in FIG. 12 that microorganisms having the ability to decompose furfuryl alcohol are present in the intestine of a termite.

Example 16

(Acquisition of isolated strain using furfuryl alcohol)

The medium (containing grown bacteria) obtained by culture in the M9 medium (further containing 0.02% furfuryl alcohol and 0.05% yeast extract) in Example 15 was coated on the surface of a tetrahydrofuran-containing M9 medium (containing 0.05% furfuryl alcohol and 1.2% agar), followed by culture at 30° C. The colonies which grew well on the medium were collected to obtain an isolated strain. Examination of the mycological character of a portion of the isolated strain showed the same results as those of the KK01 strain obtained in Example 5. The isolated strain was thus identified as the KK01 strain.

Example 17

(Screening by cumaran)

Figure 13:
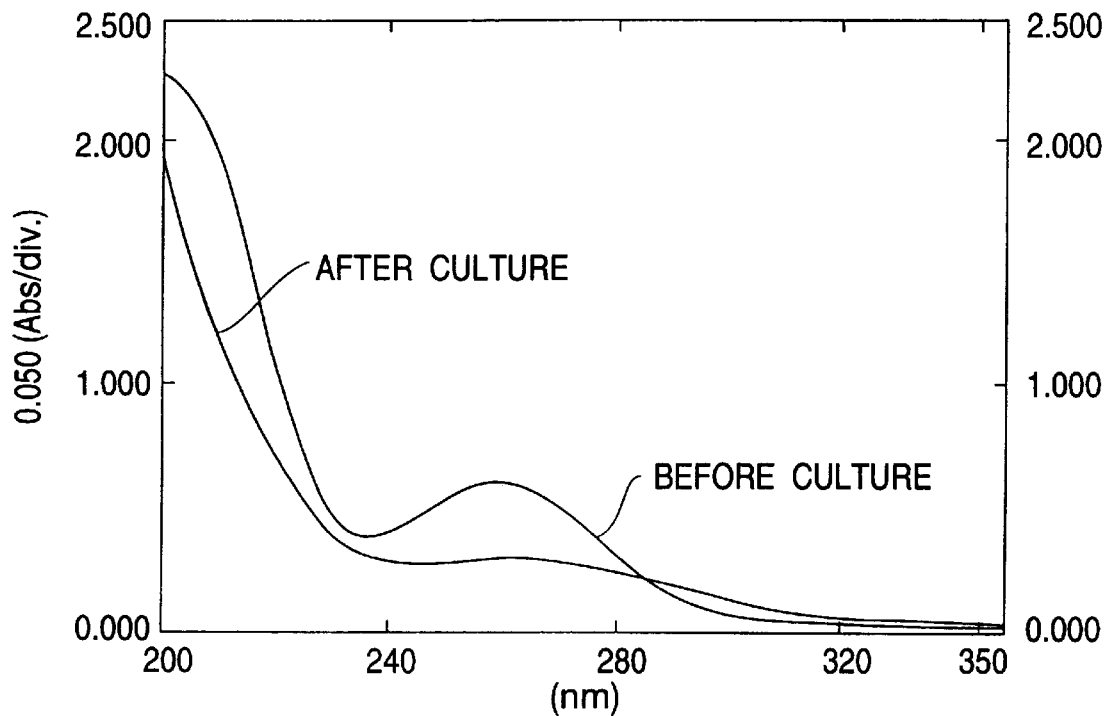
FIG. 13 is a graph showing a difference in the ultraviolet absorption spectra of a culture solution measured before and after culture in Example 17.

Microorganisms having the ability to decompose cumaran were isolated from the intestines of termites by the same method as that employed in Example 11 except that cumaran was used in place of furfural. The absorbance (200 to 350 nm) of the medium was measured before and after culture. The results obtained are shown in FIG. 13. It was confirmed by the results shown in FIG. 13 that microorganisms having the ability to decompose cumaran are present in the intestine of a termite.

Example 18

(Acquisition of isolated strain using cumaran)

The medium (containing grown bacteria) obtained by culture in the M9 medium (further containing 0.02% cumaran and 0.05% yeast extract) in Example 15 was coated on the surface of a tetrahydrofuran-containing M9 medium (containing 0.05% cumaran and 1.2% agar), followed by culture under aerobic conditions at 30° C. The colonies grown well on the medium were collected to obtain an isolated strain. Examination of the mycological characters of a portion of the isolated strain showed the same results as those of the KK01 strain obtained in Example 5. The isolated strain was thus identified as the KK01 strain.

Example 19

(Generation of 2-furan carboxylic acid)

Figure 14:
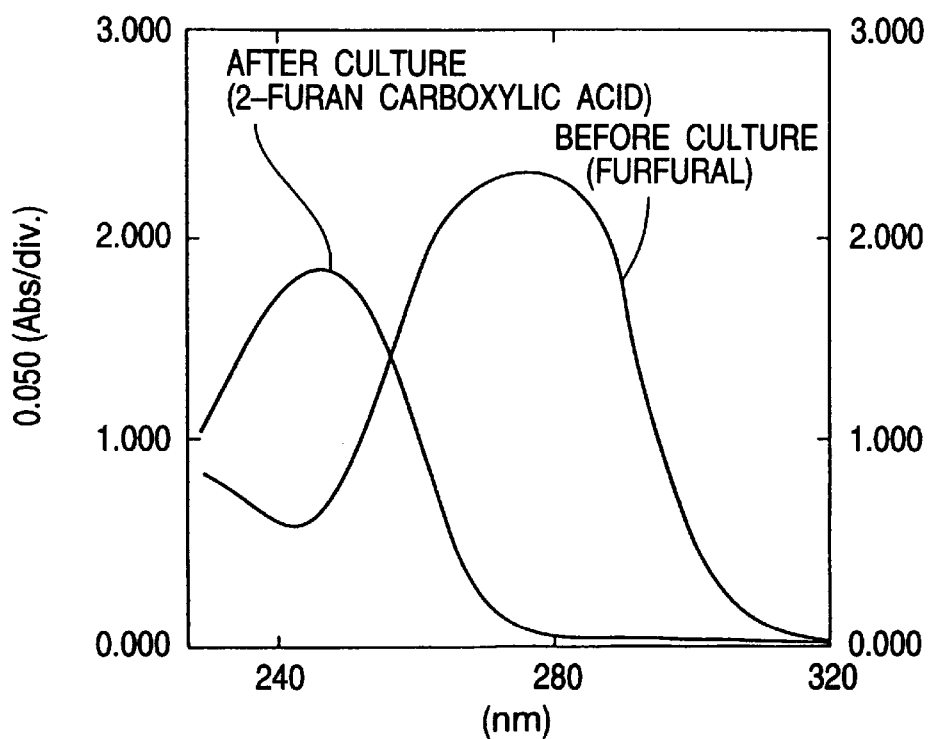
FIG. 14 is a graph showing a difference in the ultraviolet absorption spectra of a culture solution measured before and after culture in Example 19.

The KK01 strain obtained in Example 12 was cultured in a M9 medium (5 ml) containing 0.05% furfural and 0.05% yeast extract at 30° C. for 10 days. The absorbance (230 to 320 nm) of the medium was measured before and after culture. In order to perform the measurement, the medium was filtered through a filter of 0.22 μm after culture and the filtrate was then measured. The results obtained are shown in FIG. 14. As is obvious from the results shown in FIG. 14, furfural is converted to 2-furan carboxylic acid by culture of the KK01 strain.

Example 20

(Decomposition of tetrahydrofuran)

Figure 15:
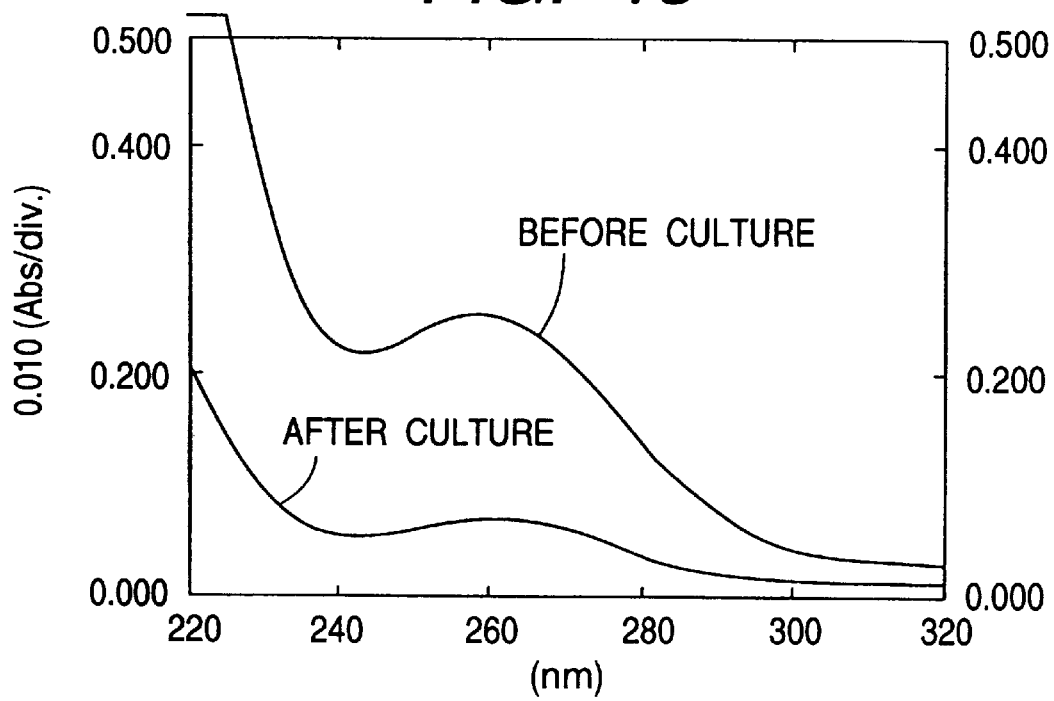
FIG. 15 is a graph showing a difference in the ultraviolet absorption spectra of a culture solution measured before and after culture in Example 20.

The KK01 strain was cultured by the same method as that employed in Example 19 except that tetrahydrofuran was used in place of furfural. The absorbance (220 to 320 nm) of the medium was measured. The results obtained are shown in FIG. 15. As is obvious from the results shown in FIG. 15, tetrahydrofuran is decomposed by a culture of the KK01 strain.

Example 21

(Decomposition of furfuryl alcohol)

Figure 16:
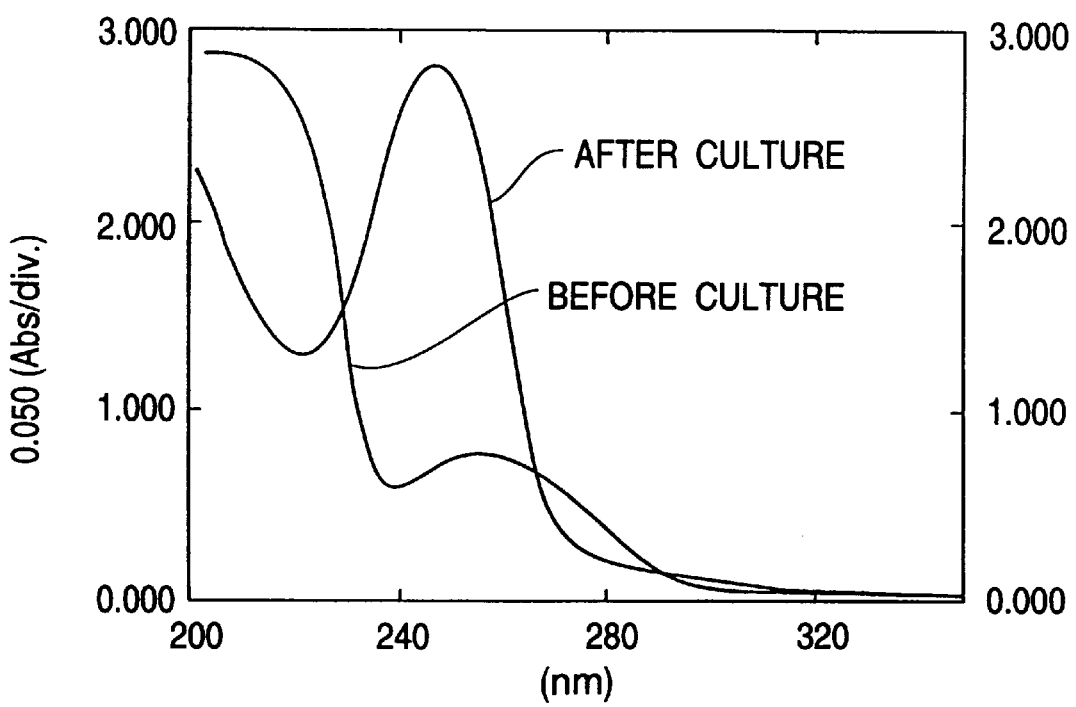
FIG. 16 is a graph showing a difference in the ultraviolet absorption spectra of a culture solution measured before and after culture in Example 21.

The KK01 strain was cultured by the same method as that employed in Example 19 except that furfuryl alcohol was used in place of furfural. The absorbance (200 to 350 nm) of the medium was measured. The results obtained are shown in FIG. 16. As is obvious from the results shown in FIG. 16, furfuryl alcohol is decomposed by a culture of the KK01 strain.

Example 22

(Decomposition of cumaran)

Figure 17:
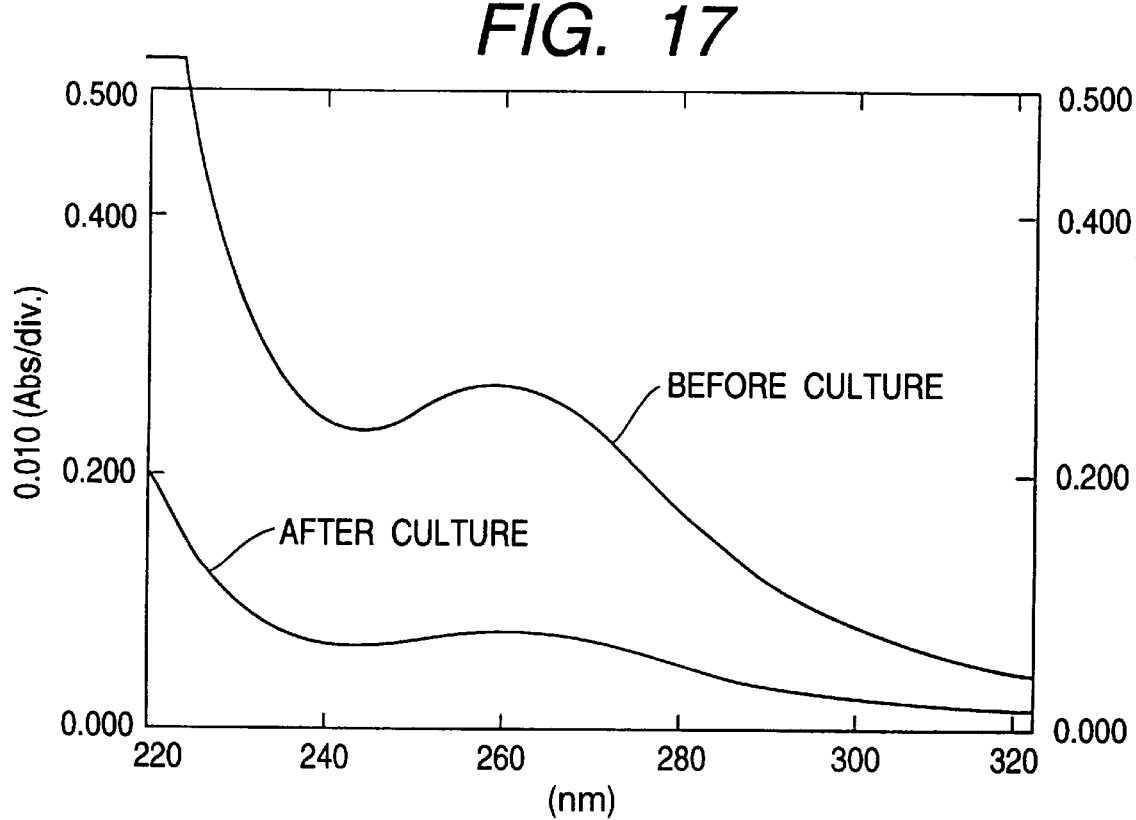
FIG. 17 is a graph showing a difference in the ultraviolet absorption spectra of a culture solution measured before and after culture in Example 22.

The KK01 strain was cultured by the same method as that employed in Example 19 except that cumaran was used in place of furfural. The absorbance (220 to 320 nm) of the medium was measured. The results obtained are shown in FIG. 17. As is obvious from the results shown in FIG. 17, cumaran is decomposed by a culture of the KK01 strain.

As seen from the above results, the strain obtained in the present invention has the ability to decompose the furan compounds, and this property is not observed in generally known strains of *Pseudomonas cepacia*.

The KK01 strain can be cultured in a medium which is generally used for bacteria Pseudomonas. Although the strain can be grown adequately in a medium containing as a single carbon source phenol, cresol or a furan compound, glucose can also appropriately be used. For example, peptone can be used as a nitrogen source singly or in combination with other substances. The yeast extract, potassium primary phosphate, ammonium chloride and the like may be added according to demand. The culture can be made under aerobic conditions, and either liquid culture or solid culture may be made. The culture temperature is preferably 30° C.

Example 23

A synthetic waste water having the composition below was synthesized, and the KK01 strain was inoculated into the waste water, followed by culture under aerobic conditions at 30° C. The changes with time of the amount of the furan compound contained in the medium were determined by measuring the ultraviolet absorption of the medium. A sample of the medium was filtered by through filter of 0.22 μm and the filtrate was then measured.

Synthetic waste water composition:

| | |
|---|---|
| Tetrahydrofuran | 50 mg |
| Furfural | 50 mg |
| Furfuryl alcohol | 50 mg |
| Cumaran | 50 mg |
| NH$_4$Cl | 200 mg |
| KH$_2$PO$_4$ | 272 mg |
| Na$_2$HPO$_4$ | 284 mg |
| Water | 1 l |
| pH (7.0) | |

Figure 18:
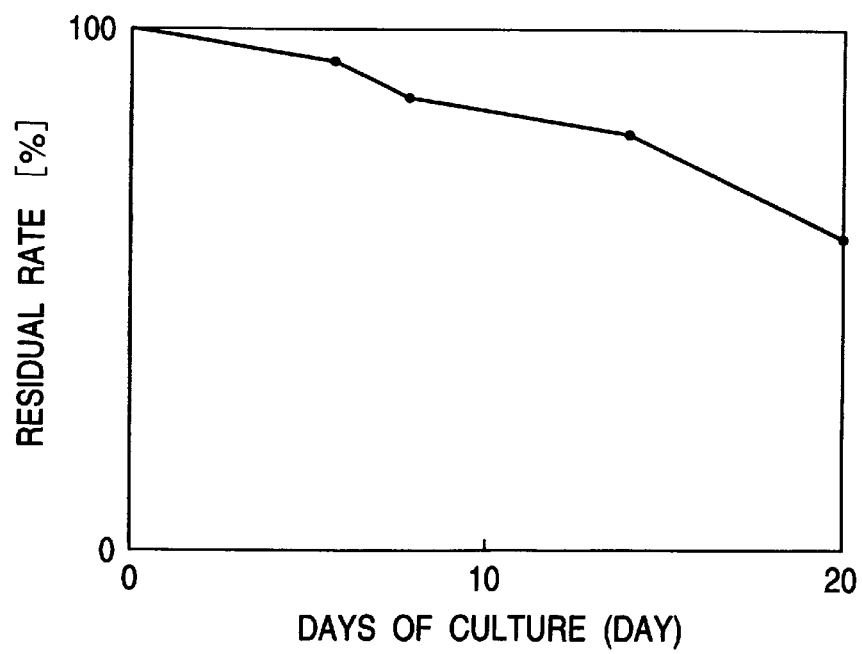
FIG. 18 is a graph in which a change with time of the amount of a furan compound in a culture medium measured in Example 23 is shown by a residual rate relative to the amount before culture which is considered as 100%.

The results obtained are shown in FIG. 18. The results shown in FIG. 18 reveal that the KK01 strain has the ability to decompose the furan compounds contained in the synthetic waste water.

The present invention establishes a method of obtaining microorganisms from the intestine of a termite having the ability to decompose phenolic compounds or furan compounds. The microorganisms obtained were suitable for biologically decomposing the phenolic compounds or furan compounds contained in the waste water.

The use of the microorganisms obtained by the above described method permits efficient biological treatment of waste water containing phenolic compounds or furan compounds which are not easily decomposed under natural conditions. This is particularly advantageous since microorganisms having the ability to decompose cresol, tetrahydrofuran and cumaran have to date not been reported. The present invention enables biological decomposition of these compounds contained in waste water. The present invention also enables biological decomposition of various chemical substances such as phenolic compounds, furan compounds and the like using a single strain.

Example 24

(The degradation of TCE by microorganisms derived from intestines of termites, and a method for obtaining the microorganisms having a TCE degrading ability from the termites)

Figure 19:
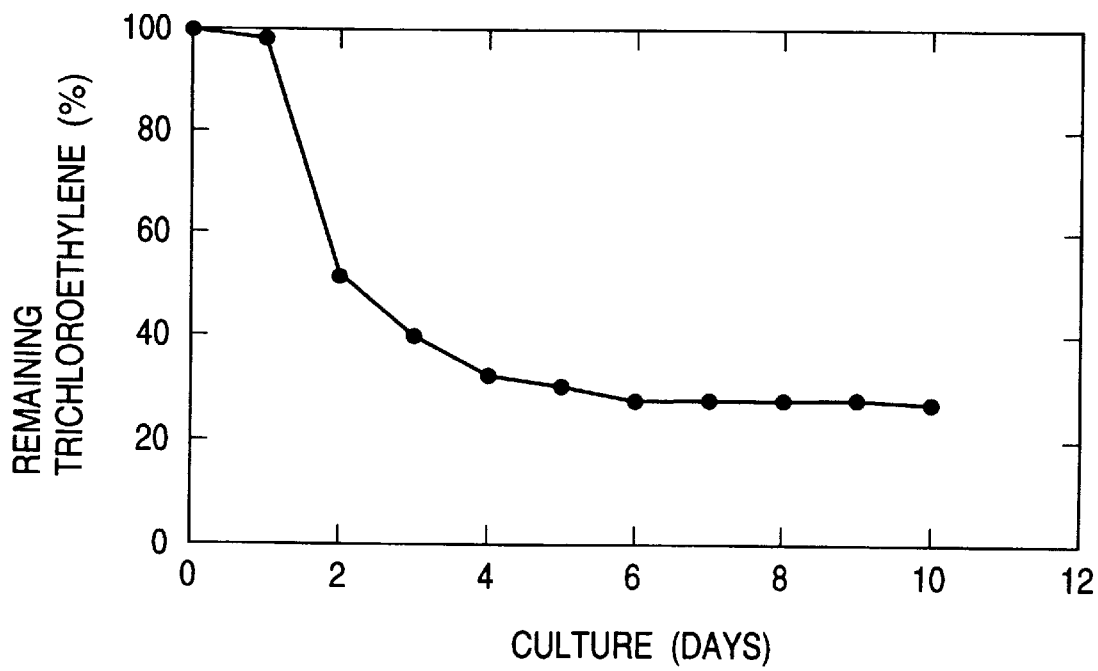
FIG. 19 shows the change by day of a ratio of remaining TCE in Example 24.

Ten workers termites of *Nasutitermes takasagoensis* were put in a culture dish, and ethyl alcohol (95%) was then poured thereinto to sterilize the surfaces of the termites. Next, the termites were washed twice with an M9 culture medium containing 0.6 ppm of TCE to remove ethyl alcohol from the surfaces. After the washing, intestines were taken out of the termites, and then crushed in the M9 culture medium containing 0.6 ppm of TCE to obtain a liquid mixture containing the crushed intestines. Next, a part of this mixture was inoculated into an M9 culture medium containing 3 ppm of TCE, 10 ppm of phenol and 0.5% of yeast extract, and then cultured at 30° C. under aerobic conditions. At the time of the passage of predetermined culture days, the culture medium was sampled and then filtered, and the amount of TCE in the resultant filtrate was measured in a usual manner and ratios of remaining TCE corresponding to the culture days were calculated. The obtained results are shown in FIG. 19. In this case, the amount of TCE at the beginning of the cultivation was regarded as 100%. The results indicate that the microorganisms having the TCE degrading ability can be obtained from the intestines of the termites.

Example 25

(Acquisition of isolated bacterium strain having TCE degrading ability, and degradation of TCE)

A culture medium (including grown bacteria) obtained by culturing an M9 culture medium (further including 3 ppm of TCE, 10 ppm of phenol and 0.05% of yeast extract) of Example 1 was applied onto the surface of a TCE-containing M9 agar culture medium (including 3 ppm of TCE, 50 ppm of phenol and 1.2% of agar), and then cultured at 30° C. for 2 days. Some colonies were formed on the agar culture medium, and each of these colonies was inoculated into an M9 culture medium (5 ml) containing 0.6 ppm of TCE, 10 ppm of phenol and 0.05% of yeast extract and then cultured at 30° C. for 2 days.

Next, necessary numbers of serum bottles were prepared in which 30 ml of an M9 culture medium containing 3 ppm of TCE, 10 ppm of phenol and 0.05% of yeast extract was placed, and each culture medium (0.1 ml) of the bacteria collected from each of the above-mentioned colonies was inoculated into each of the above-mentioned serum bottles. Afterward, the serum bottles were completely sealed with butyl rubber septums and aluminum seals, followed by cultivation at 30° C. At the time of the passage of predetermined culture days, the amount of TCE in each serum bottle was quantitatively analyzed by a headspace method using gas chromatography, and the microorganisms in the serum bottle in which TCE had been degraded were regarded as the isolated strain of TCE degrading bacteria.

For one of the isolated strains, bacteriological characteristics were inspected, and consequently, the following results were obtained. It has been confirmed that this isolated strain was the same as a strain KK01 (International Deposition No. FERM BP-4235) which was deposited as a novel strain having the ability to degrade phenolic compounds such as phenol, o-cresol, m-cresol and p-cresol in Fermentation Research Institute, Agency of Industrial Science and Technology, Ministry of International Trade and Industry on Mar. 11, 1992 and then changed to the international deposition in accordance with a Budapest treaty on Mar. 9, 1993.

A. Morphological Properties (1) Gram stain: Negative
(2) Size and shape of the bacteria: Bacillus having a length of 1.0–2.0 µm and a width of about 0.5 µm.

(3) Mobility: Present

B. Growth state of the bacteria in each culture medium.

| Culture Medium | Culture Temp. (° C.) | Growth State |
|---|---|---|
| Blood agar culture medium | 37 | + |
| Lactose agar culture medium | 37 | + |
| Chocolate agar culture medium | 37 | ++ |
| GMA | 37 | − |
| Scyllo | 37 | − |
| Usual agar culture medium | 4 | − |
| Usual agar culture medium | 25 | ± |
| Usual agar culture medium | 37 | − |
| Usual agar culture medium | 41 | ± |

C. Physiological properties (1) Aerobic or anaerobic: Strictly aerobic
(2) Degradation type of saccharose: Oxidation type
(3) Production of oxidase: +
(4) Reduction of silver nitrate: +
(5) Production of hydrogen sulfide: −
(6) Production of indole: −
(7) Production of urease: −
(8) Liquefaction of gelatin: −
(9) Hydrolysis of arginine: −
(10) Decarboxylation of lysine: +
(11) Decarboxylation of ornithine: −
(12) Utilization of citric acid: +
(13) Methylcarbinolacetyl reaction (VP reaction): −
(14) Detection of tryptophane deaminase: −
(15) ONPG: −
(16) Utilization of carbohydrates:
  Glucose: +
  Fruit sugar: +
  Maltose: +
  Galactose: +
  Xylose: +
  Mannitol: +
  White sugar: −
  Lactose: +
  Aesculin: −
  Inositol: −
  Sorbitol: −
  Rhamnose: −
  Melibiose: −
  Amygdalin: −
  L-(+)-arabinose: +

Next, this strain KK01 was inoculated into an M9 culture medium (5 ml) containing 0.6 ppm of TCE, 10 ppm of phenol and 0.05% of yeast extract, and then cultured at 30° C. for 2 days.

Afterward, 30 ml of an M9 culture medium containing 3 ppm of TCE, 10 ppm of phenol and 0.05% of yeast extract was placed in a serum bottle, and 0.1 ml of the above-mentioned strain KK01 culture medium was inoculated into the M9 culture medium in the serum bottle. Afterward, the serum bottle was crimp-sealed with a butyl rubber septum and an aluminum seal, followed by cultivation at 30° C.

Figure 20:
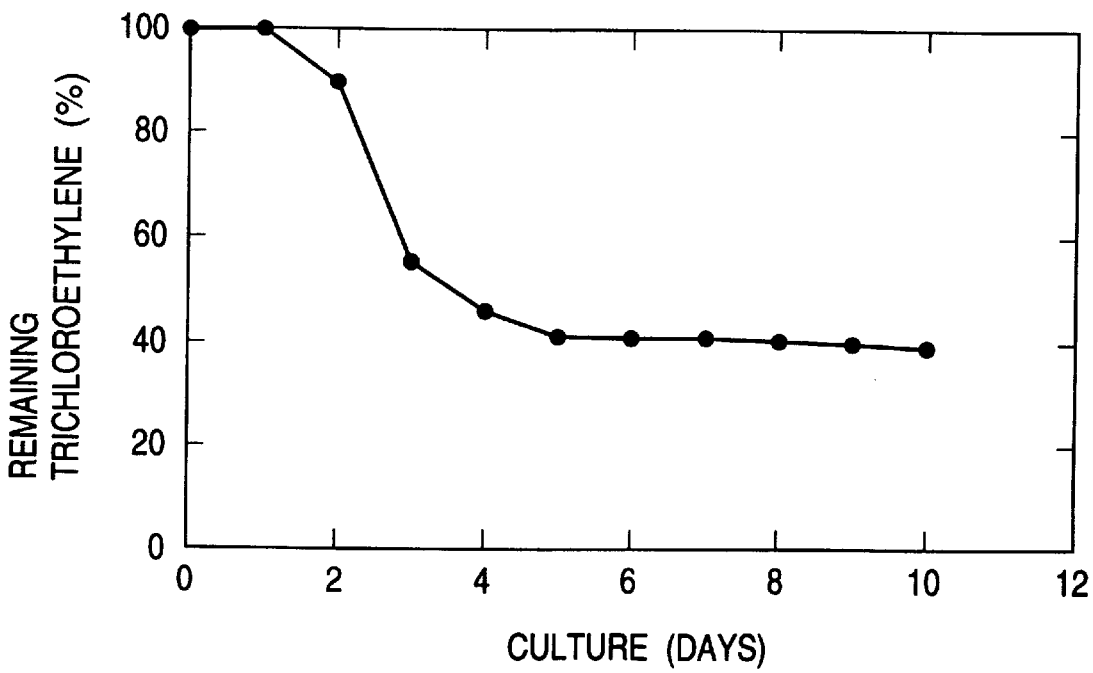
FIG. 20 shows the change by day of a ratio of remaining TCE in a serum bottle in Example 25.

At the time of the passage of predetermined culture days, the amount of TCE in the serum bottle was quantitatively analyzed by a headspace method using gas chromatography, and ratios of remaining TCE corresponding to the culture days were determined. The obtained results are shown in FIG. 20. In this case, the amount of TCE at the beginning of the cultivation was regarded as a residual ratio of 100%.

Example 26

(Remediation of a soil by bacteria derived from intestines of termites)

Ten workers termites of

Figure 21:
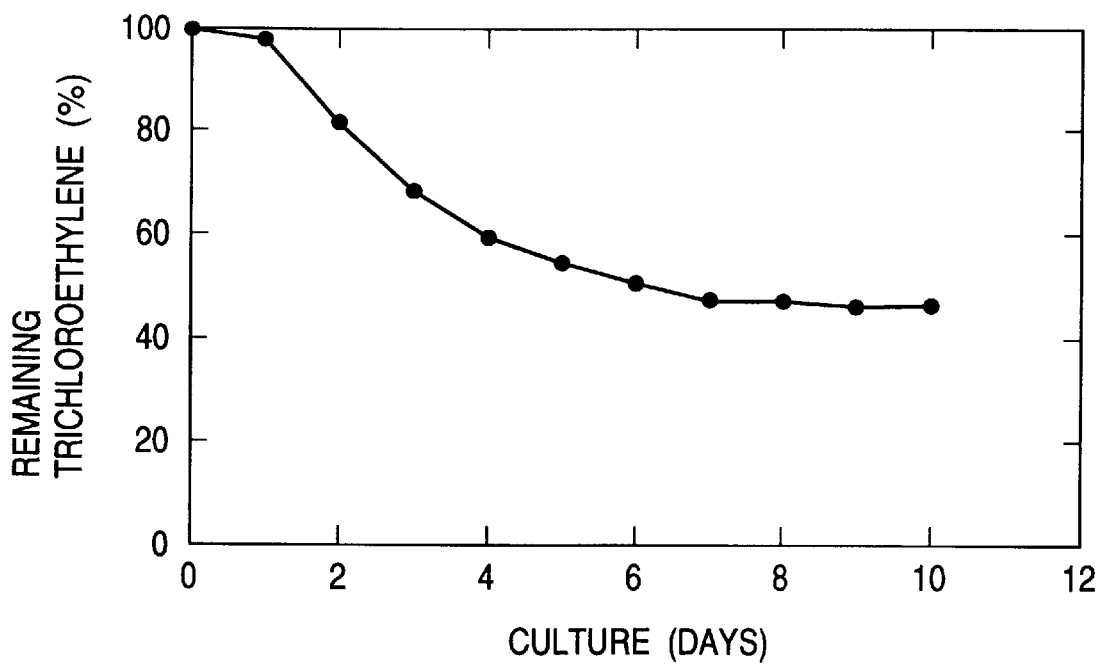
FIG. 21 shows the change by day of a ratio of remaining TCE in a serum bottle in Example 26.

Nasutitermes takasagoensis were put in a laboratory dish, and ethyl alcohol (95%) was then poured thereinto to sterilize the surfaces of the termites. Next, the termites were washed twice with an M9 culture medium containing 0.6 ppm of trichloroethylene (TCE) to remove ethyl alcohol from the surfaces. After the washing, intestines were taken out of the termites, and then crushed in the M9 culture medium containing 0.6 ppm of TCE to obtain a liquid mixture containing the crushed intestines. Next, 30 ml of a culture medium (an M9 culture medium containing 3 ppm of TCE, 10 ppm of phenol and 0.5% of yeast extract) was placed in a serum bottle, and a sterilized soil was then added thereto till a water surface. Afterward, a part of the liquid mixture containing the crushed intestines was inoculated into the soil, and the serum bottle was then completely sealed with a butyl rubber septum and an aluminum seal, followed by cultivation at 30° C. At the time of the passage of predetermined culture days, the amount of TCE in the serum bottle was quantitatively analyzed by a headspace method using gas chromatography, and ratios of remaining TCE corresponding to the culture days were determined. The obtained results are shown in FIG. 21. In this case, the amount of TCE at the beginning of the cultivation was regarded as a residual ratio of 100%.

Example 27

A strain KK01 was inoculated into an M9 culture medium (5 ml) containing 0.6 ppm of TCE, 10 ppm of phenol and 0.05% of yeast extract, and then cultured at 30° C. for 2 days.

Next, 30 ml of an M9 culture medium containing 3 ppm of TCE, 10 ppm of phenol and 0.5% of yeast extract was placed in a serum bottle, and a sterilized soil was then added thereto till a water surface. Afterward, 0.1 ml of the above-mentioned strain KK01 culture medium was inoculated into the M9 culture medium, and the serum bottle was then crimp-sealed with a butyl rubber septum and an aluminum seal, followed by cultivation at 30° C.

Figure 22:
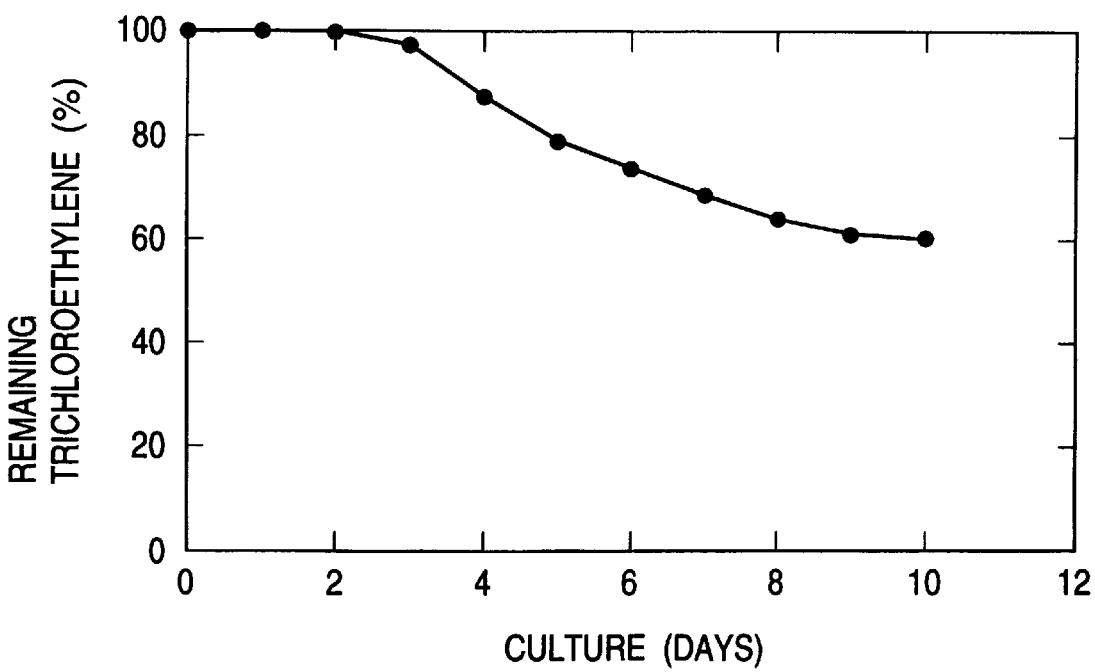
FIG. 22 shows the change by day of a ratio of remaining TCE in a serum bottle in Example 27.

At the time of the passage of predetermined culture days, the amount of TCE in the serum bottle was quantitatively analyzed by a headspace method using gas chromatography, and ratios of remaining TCE corresponding to the culture days were determined. The obtained results are shown in FIG. 22. In this case, the amount of TCE at the beginning of the cultivation was regarded as a residual ratio of 100%.

Example 28

A strain KK01 was inoculated into 5 ml of a culture medium (an M9 culture medium containing 1 ppm of TCE, 0.05% of yeast extract and phenol having a predetermined concentration), and then cultured at 30° C. for 2 days.

Next, 15 ml of a culture medium (an M9 culture medium containing 1 ppm of TCE, 0.2% sodium glutamate and phenol having a predetermined concentration) was placed in a serum bottle, and 0.1 ml (inclusive of bacteria) of the above-mentioned strain KK01 culture medium was inoculated into the culture medium in the serum bottle. Afterward, the serum bottle was then completely sealed with a butyl rubber septum and an aluminum seal, followed by cultivation at 30° C. Next, 0.1 ml of the gaseous phase in the serum bottle was sampled with time, and then analyzed by gas chromatography (Gas Chromatogram GC-9AM; made by Shimazu Seisakusho Ltd.).

Furthermore, the culture medium was sampled, and an absorbance (660 nm) of the culture medium was then measured by a spectrophotometer to determine the number of the bacteria.

Figure 23:
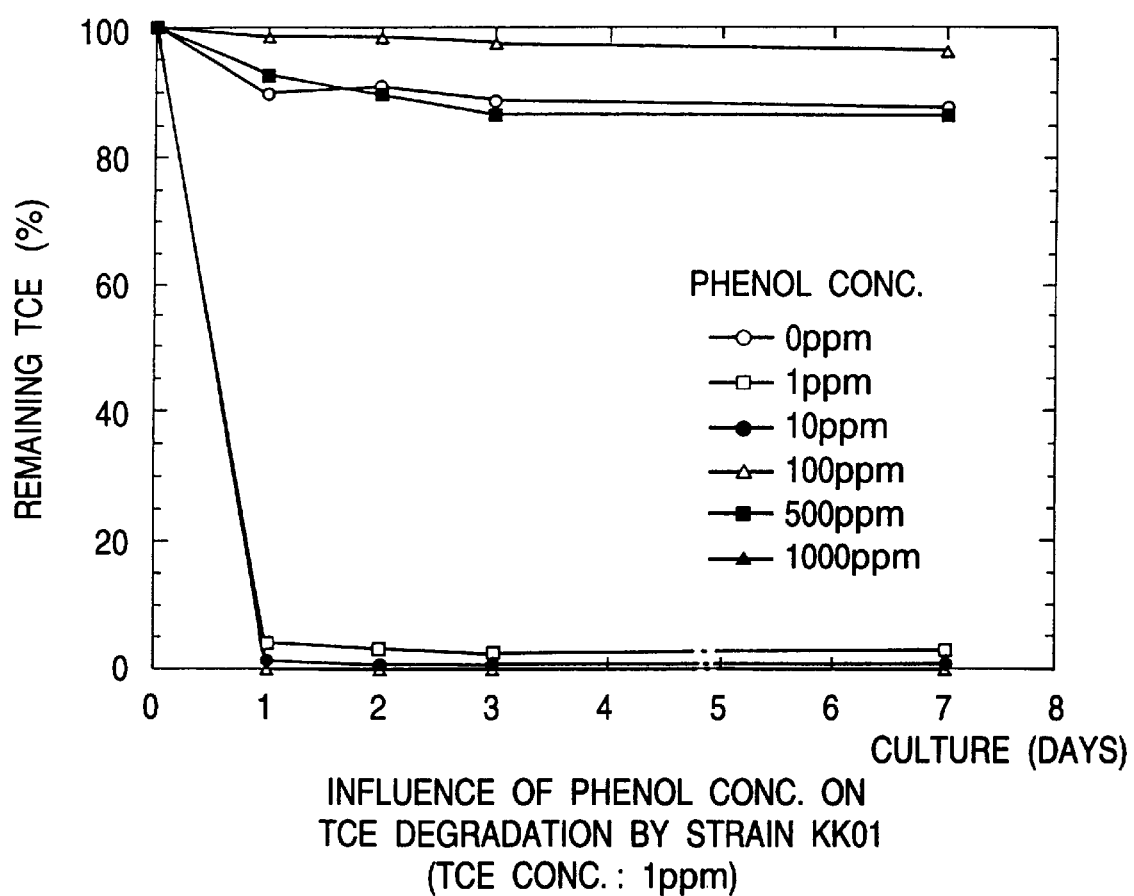
FIG. 23 shows the influence of phenol concentration on TCE degradation in Example 28.
Figure 24:
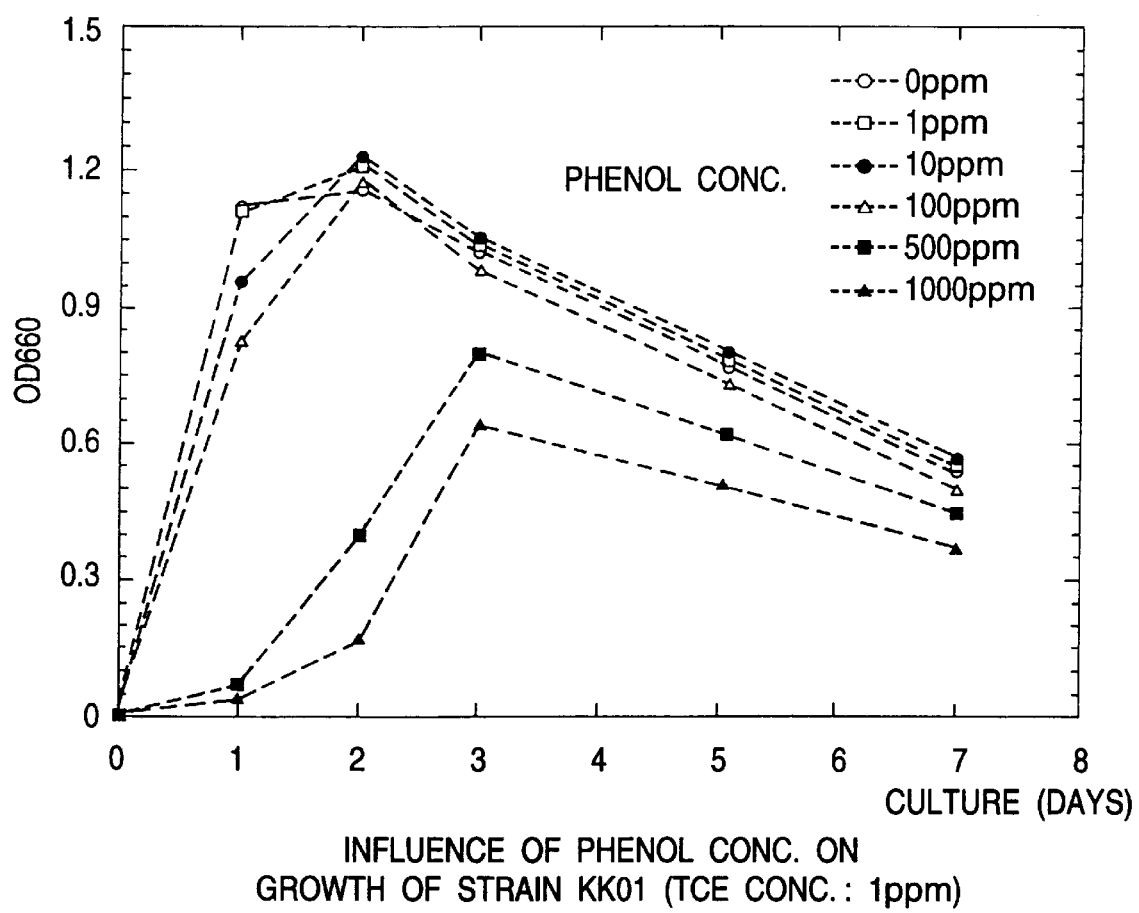
FIG. 24 shows the influence of phenol concentration on the growth of a strain KK01 in Example 28.

In the case that the concentration of phenol which was the inducer was set to 0, 1, 10, 100, 500 and 1,000 ppm, the change of ratios of remaining TCE (which were determined by regarding the amount of TCE at the beginning of the cultivation as 100%) was shown in FIG. 23, and the change of optical density (O.D.) indicating a bacteria number is shown in FIG. 24.

Here, phenol which can be used as the inducer accelerates assimilability as a nutrition for the bacteria to be activated and the expression of a TCE degrading enzyme accompanied thereby, but on the other hand, phenol also inhibits the growth of the bacteria, when its amount is too large.

Therefore, it is necessary to determine the maximum amount of phenol in the range in which the bacteria are not damaged and the degradation activity of the bacteria is increased as much as possible.

FIG. 24 indicates that in the case of a phenol concentration of zero (no phenol is added), the bacteria number increases to O.D.=1.13 in the vicinity of a substantially maximum value (O.D.=1.17 on the second day) on the first culture day, and after the third day, O.D. decreases gradually. This shows the ideal bacteria growth without the hindrance to bacteria growth by phenol. At this time, however, the TCE-degrading enzyme is not expressed, so that the TCE degradation does not occur (FIG. 5).

When the phenol concentration is 1 ppm, O.D. on the first day is 1.12 and O.D. on the second day is a maximum value, i.e., 1.21, and therefore the growth characteristics of the bacteria are scarcely different from the case where the phenol concentration is zero. However, it is apparent that the TCE degradation is drastically improved (FIG. 23). When the phenol concentration is increased up to 10 ppm and 100 ppm, O.D. on the first day is 0.96 (O.D. on the second day is a maximum value, 1.23) and 0.83 (O.D. on the second day is a maximum value, 1.18), respectively, and the growth of the bacteria is gradually hindered on the first day. However, the culture days giving the maximum bacteria number and its maximum value scarcely change within the phenol concentration range of 0 to 100 ppm, and with regard to the decrease of O.D. after the maximum value, the very similar results are shown.

In addition, it is also apparent from FIG. 23 that TCE is also degraded successively.

Particularly in the case of 100 ppm, the degradation proceeded substantially 100%, i.e., up to a detection limit or less of a detector [FID detector (flame ionization detector)] in one day.

On the other hand, when the phenol concentration was 500 ppm and 1,000 ppm, the degradation of TCE did not occur so much. At this time, the growth of the bacteria was noticeably hindered, judging from the fact that O.D. values on the first day at the above-mentioned phenol concentrations were 0.07 and 0.03, respectively. According to the investigation of correlation between various culture growth curves and the ability to degrade TCE and the like, when a culture curve at an early stage till the days giving the maximum O.D. value with respect to the days of the culture shows a substantially convex form, the activity of the bacteria can be heightened. That is, when the microorganisms were cultured by a batch system in the presence of the inducer and the growth curve of the microorganisms is close to y=f(t) (wherein y is a bacteria number determined with an optical density (O.D.), and t is a culture time), and if the concentration of the inducer is set to a value in a range which meets the formula $$2\int_0^T f(t)dt - T \cdot f(T) \geq 0$$

(wherein T is a culture time when the bacterial number y is maximum),
the activity of the bacteria can be heightened. More preferably, if the concentration of the inducer is set to the maximum value in this range, the activity of the bacteria per unit amount of the bacteria can be maximized.

If even a small amount of the inducer is contained, it can be presumed that the degradation activity of the bacteria can be enhanced and the biodegradation proceeds. However, from a practical viewpoint, a ratio of the concentration of the inducer to that of the chlorinated organic compound to be degraded is preferably 0.2 or more, more preferably 0.5 or more. Moreover, when the concentration of the chlorinated organic compound is as high as 5 ppm or more, the inducer is used in a ratio of 1 or more so as to obtain good effects.

Example 29

Figure 25:
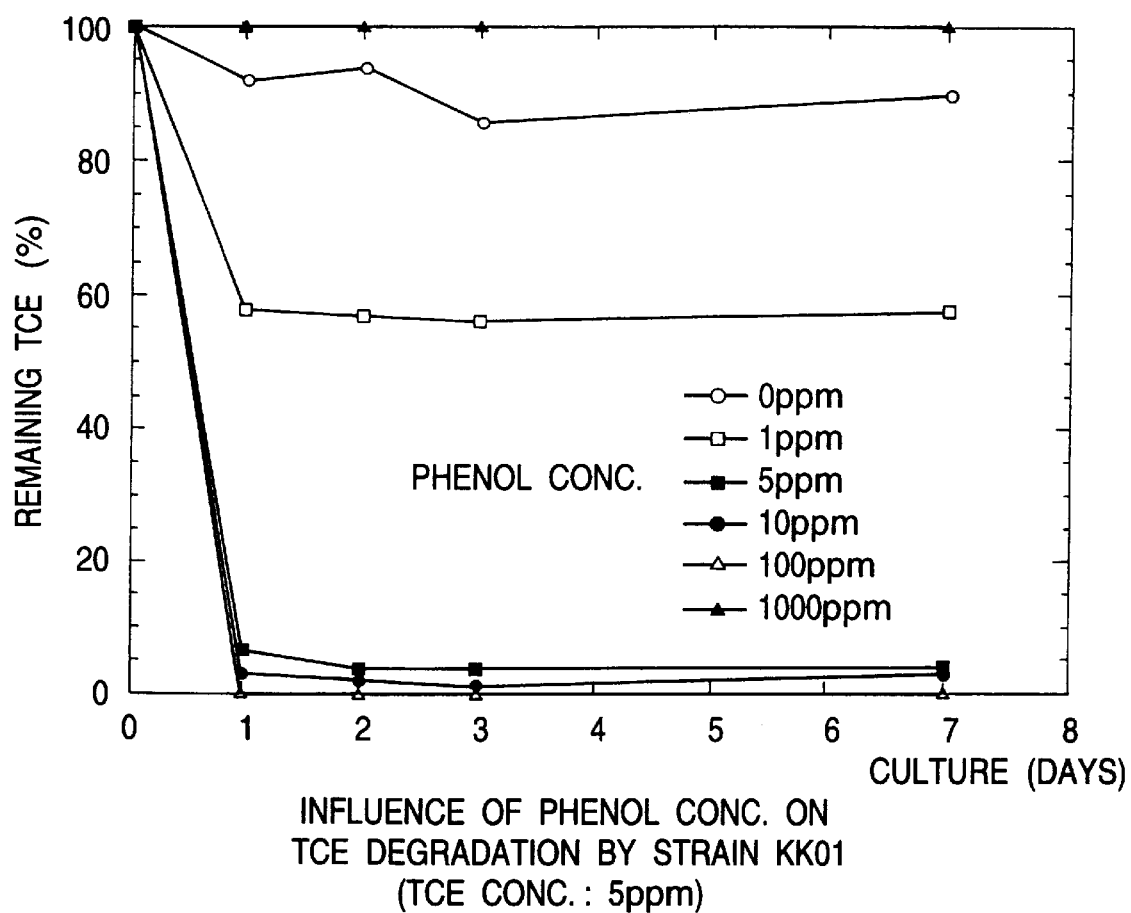
FIG. 25 shows the influence of phenol concentration on TCE degradation in Example 29.
Figure 26:
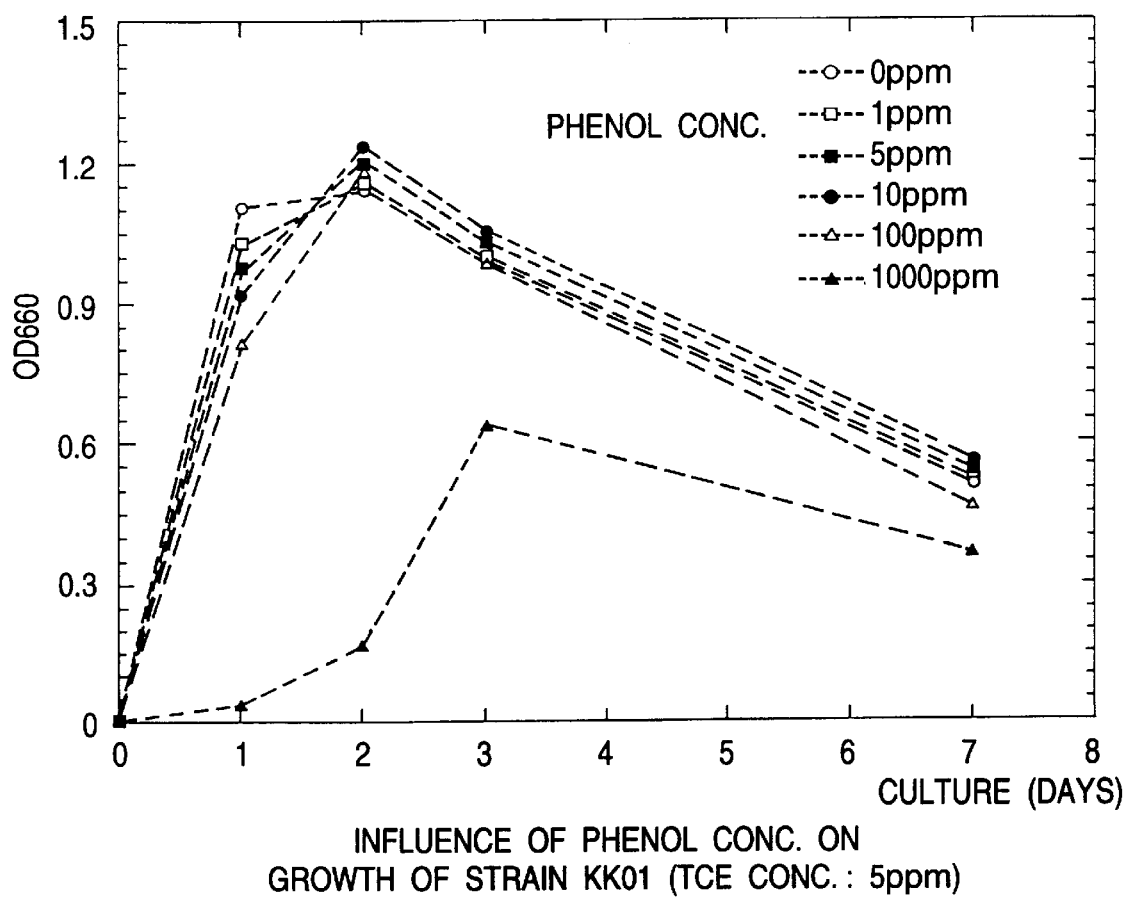
FIG. 26 shows the influence of phenol concentration on the growth of a strain KK01 in Example 29.

An experiment was carried out by the same procedure as in Example 5 except that the concentration of TCE which was a substance to be degraded was set to 5 ppm. The change of ratios of remaining TCE is shown in FIG. 25, and the change of O.D. indicating a bacteria number is shown in FIG. 26.

When the concentration of phenol was 100 ppm, the degradation of TCE proceeded up to a detection limit or less of an FID detector in one day. Even when the concentration of phenol was 1, 5 and 10 ppm, degradations of about 62, 93 and 97% were observed in one day, respectively. On the contrary, when no phenol was added and when the phenol concentration was 1,000 ppm, the degradation of TCE was scarcely observed.

On the other hand, with regard to the growth of the bacteria, when the phenol concentration was 100 ppm or less, all of initial growth curves showed a convex form, and a maximum bacteria number (O.D.=about 1.2) was reached in two culture days. When the phenol concentration was 1,000 ppm, the bacteria growth was apparently hindered, and a period of one day or more were more taken to reach the maximum bacteria number than when the phenol concentration was 100 ppm.

Example 30

Cultivation was carried out by the same procedure as in Example 5 except that the concentration of TCE was set to 30 ppm. The obtained results are set forth in FIGS. 27 and 28.

Figure 27:
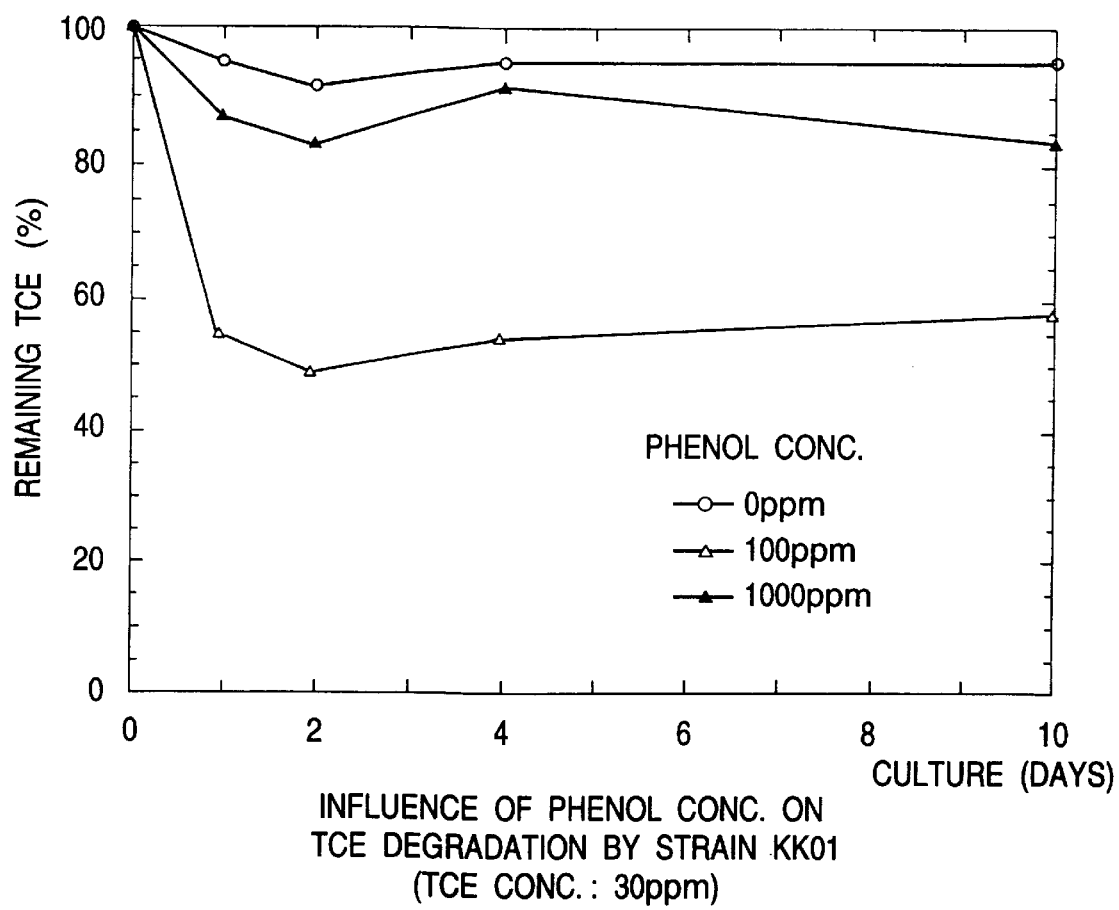
FIG. 27 shows the influence of phenol concentration on TCE degradation in Example 30.

As shown in FIG. 27, when phenol concentration was 100 ppm, a TCE degradation of about 45% was observed in one day. On the contrary, in the case of a phenol concentration of 1,000 ppm and in the case of no phenol, the degradation of TCE scarcely proceeded.

Figure 28:
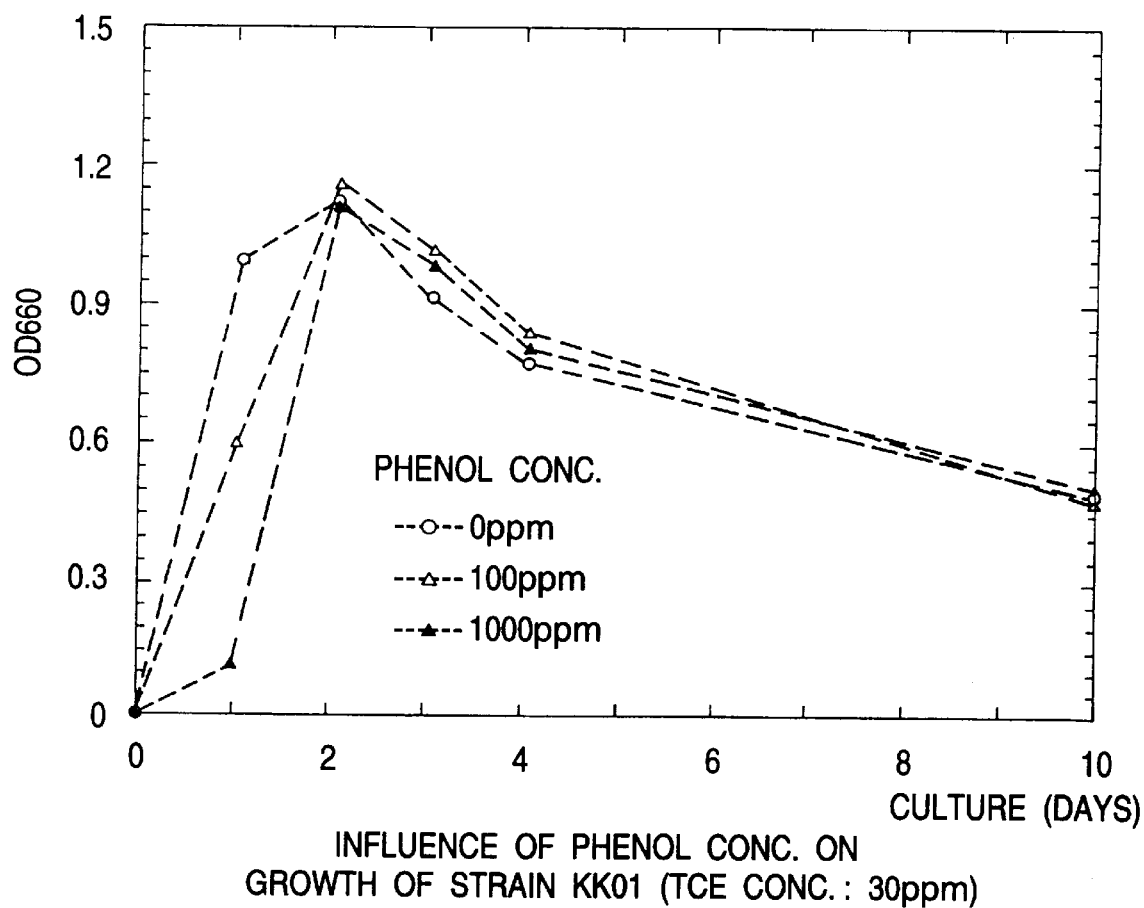
FIG. 28 shows the influence of phenol concentration on the growth of a strain KK01 in Example 30.

On the other hand, as shown in FIG. 28, bacteria growth proceeded similarly at phenol concentrations of 0 and 100 ppm. In addition, when the phenol concentration was 1,000 ppm, a maximum bacteria number and days taken to reach the maximum bacteria number were equal to cases where the phenol concentrations were 0 and 100 ppm. However, the initial bacteria growth curve in the case of the 1,000 ppm concentration did not show a convex form, which meant the hindrance of the bacteria growth.

As described above, when the phenol concentration was 1,000 ppm, the maximum bacteria number and the days taken to reach the maximum bacteria number were equal to the case where the phenol concentration was 100 ppm, but nevertheless, the degradation of TCE scarcely proceeded. This fact indicates that the bacteria numbers similarly increase at concentrations of 100 ppm and 1,000 ppm, but the activation of the bacteria degradation ability took place only in the case of 100 ppm representing the convex bacteria growth curve.

Example 31

In general, it is considered that aromatic compound-assimilating bacteria such as a Pseudomonas genus are present in a soil. Now, 1 g of a brown forest earth sampled in Kanagawa Prefecture of Japan was added to 15 ml of an M9 culture medium in which the concentration of phenol was adjusted to 200 ppm, and shake culture was then carried out at 30° C. for 3 days. Afterward, 100 µl of the thus shake-cultured medium was transferred to a similar culture medium, and then further shake-cultured at 30° C. for 3 days. This medium was plate-counted on an agar plate culture medium having a similar composition (containing 200 ppm of phenol), and as a result, bacteria of $10^6$ to $10^7$ cells/g wet soil were counted.

One gram of the soil including the confirmed aromatic compound-assimilating bacteria was added to 15 ml of an M9 culture medium in which phenol concentration and TCE initial concentration was adjusted to 200 ppm and 15 ppm, respectively, followed by shake culture at 30° C. at 120 rpm for 7 days. Afterward, a TCE degradation ratio was determined in the same manner as described above, and as a result, a TCE degradation of about 50% was observed. That is, it was confirmed that the bacteria capable of degrading TCE in the presence of phenol were present in the soil.

On the basis of the above-mentioned results, experiments were carried out to inspect the phenol concentration which had an influence on the TCE degradation of native aromatic compound-assimilating and TCE-degrading bacteria. That is, the TCE degradation per gram of the soil was measured in the same manner as in Example 28. The obtained results are shown in FIGS. 29 and 30.

Figure 29:
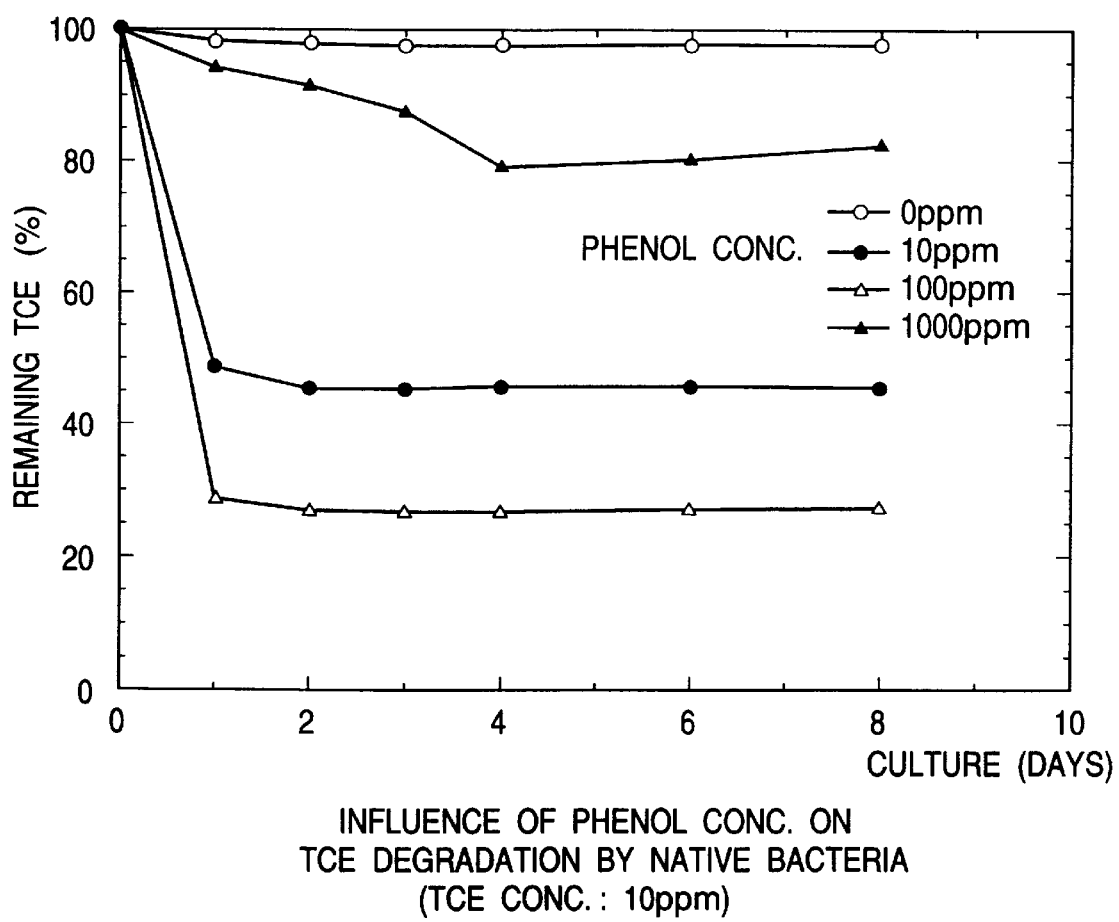
FIG. 29 shows the influence of phenol concentration on TCE degradation in Example 31.

According to the results of FIG. 29, when the phenol concentration was 100 ppm, the maximum degradation was observed, and a TCE degradation of about 70% in one day was observed. Next, when the phenol concentration was 10 ppm, a TCE degradation of about 50% in one day was observed. In addition when the phenol concentration was 1,000 ppm, the extremely slow degradation was observed.

Figure 30:
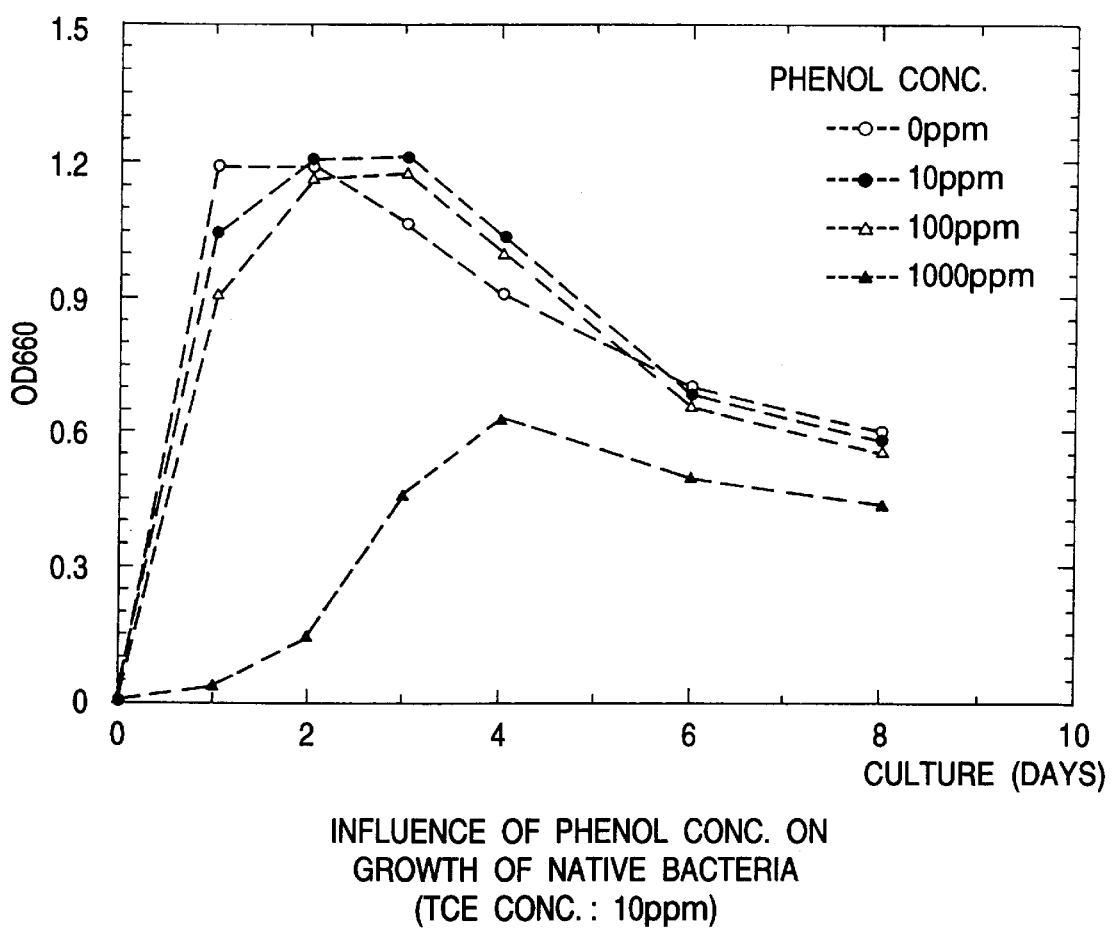
FIG. 30 shows the influence of phenol concentration on the growth of native (indigenous) bacteria in Example 31.

On the other hand, as shown in FIG. 30, with regard to the growth of the bacteria, when the phenol concentrations were 0, 10 and 100 ppm, all of their initial growth curves showed a convex conformation, as in the case of a strain KK01. However, when the phenol concentration was 1,000 ppm, the bacteria growth was definitely hindered.

Example 32

Figure 31:
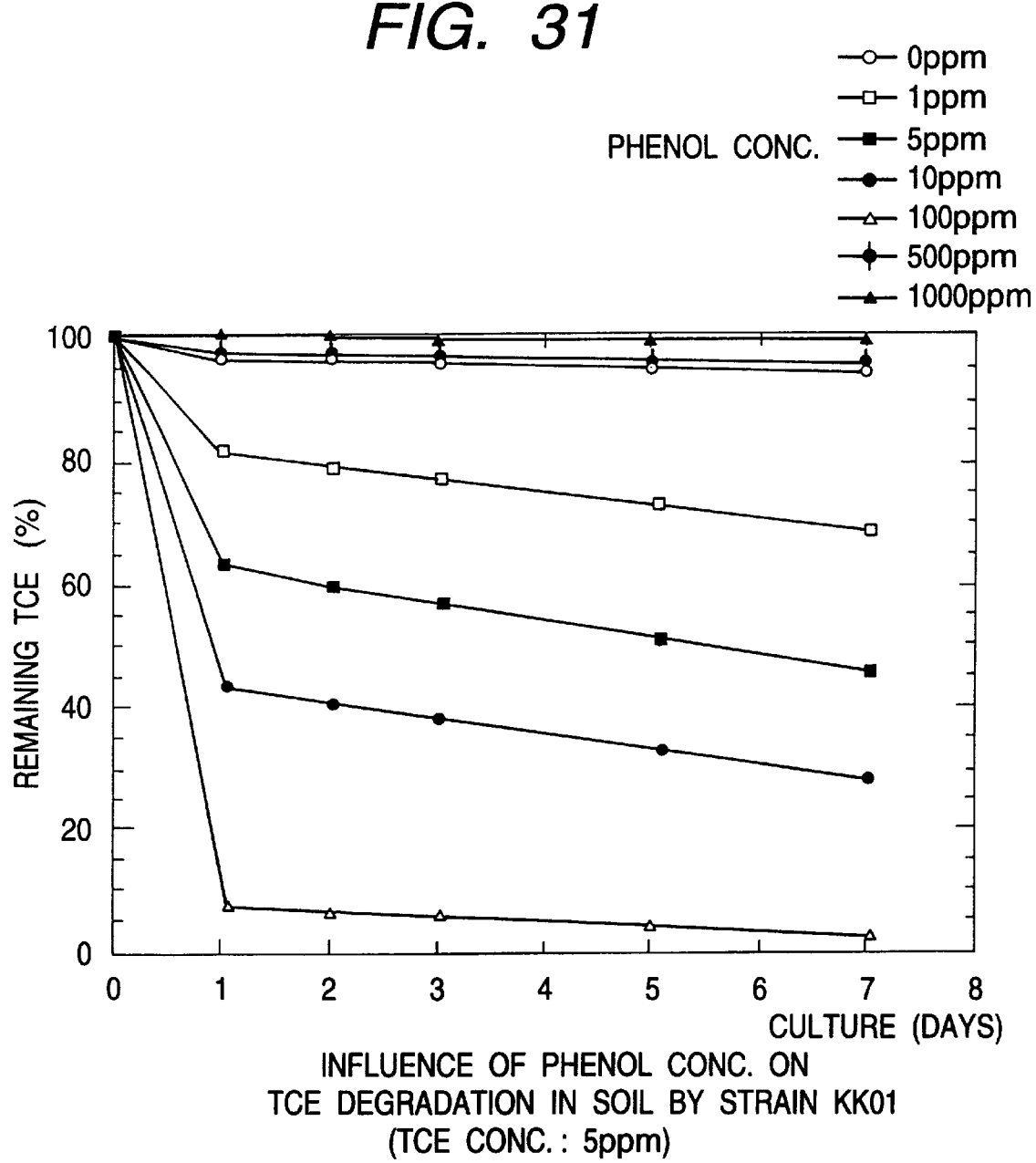
FIG. 31 shows the influence of phenol concentration on TCE degradation in Example 32.

15 ml of a culture medium [an M9 culture medium containing 0.2% sodium glutamate and phenol having each of predetermined concentrations {0, 1, 5, 10, 100, 500 and 1,000 ppm (mg/kg of a wet soil)}] and a strain KK01 (0.1 ml of a KK01 species culture medium) were added to a serum bottle containing 100 g of a sterilized loamy layer of the Kanto District polluted with TCE at 5 ppm (5 mg of TCE per kg of the wet soil) and having a moisture content of 90%, and they were then uniformly mixed. Next, the serum bottle was crimp-sealed with a butyl rubber septum and an aluminum seal, followed by stationary culture at 30° C. Afterward, 0.1 ml of the gaseous phase in the serum bottle was sampled with time, and ratios of remaining TCE were determined, as in the case of Example 28. The obtained results are shown in FIG. 31.

It can be understood that a degrading ability substantially corresponding to the case of the 5 ppm TCE culture medium system of Example 29 can be obtained also in the soil system, depending upon the concentration of phenol.

Therefore, in view of the results in Example 29 and FIGS. 25 and 26, i.e., on the basis of the data of a bacteria growth curve obtained by the experiment of a culture medium batch system, there can be set a practically effective concentration of an inducer in the case of the soil.

Example 33

The same procedure as in Example 28 was carried out except that cis-1,2-dichloroethylene (cis-DCE) was used as a material to be degraded and the concentration of this cis-DCE was set to 13 ppm. The obtained results are shown in FIGS. 32 and 33.

Figure 32:
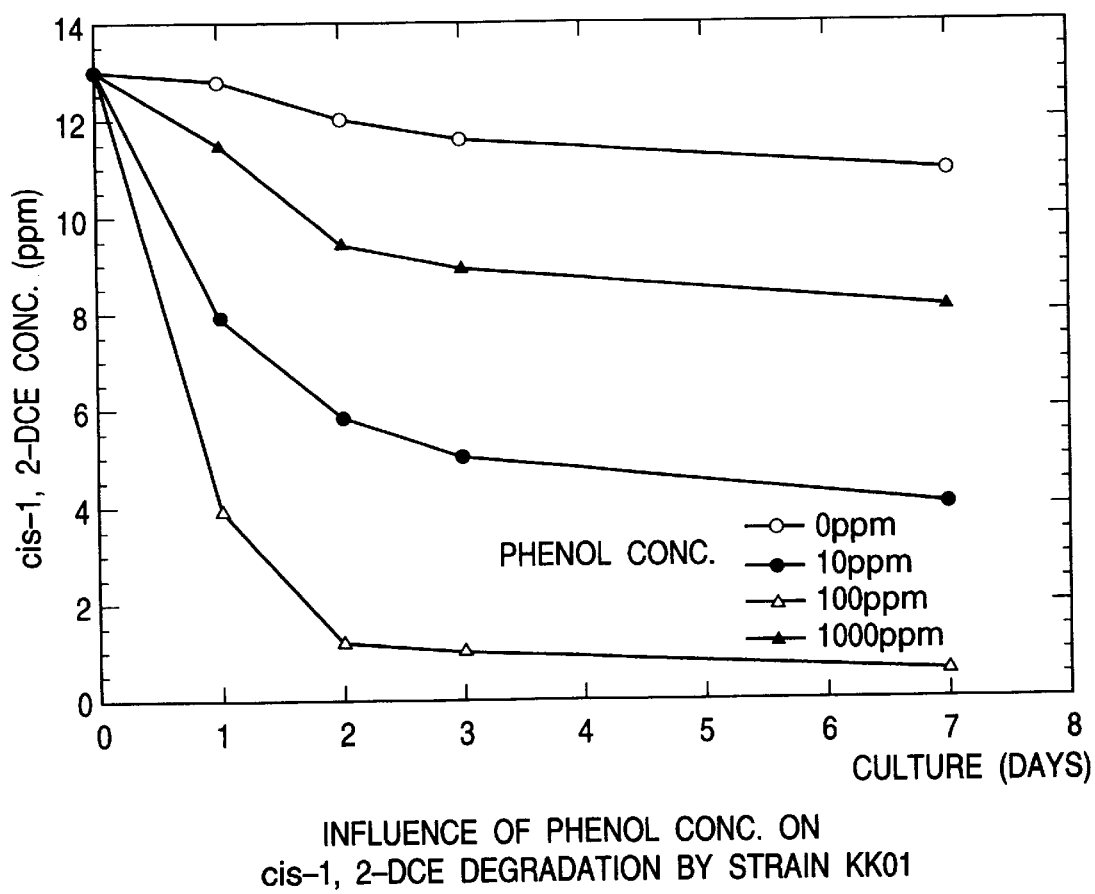
FIG. 32 shows the influence of phenol concentration on cis-DCE degradation in Example 33.

As shown in FIG. 32, when the phenol concentration was 100 ppm, cis-DCE was degraded from 13 ppm to 1 ppm or less in 7 days. On the contrary, when the phenol concentration was 10 ppm, cis-DCE was degraded only to 4 ppm in 7 days. In addition, when the phenol concentration was 1,000 ppm, cis-DCE was degraded only to 8 ppm in the same days.

Figure 33:
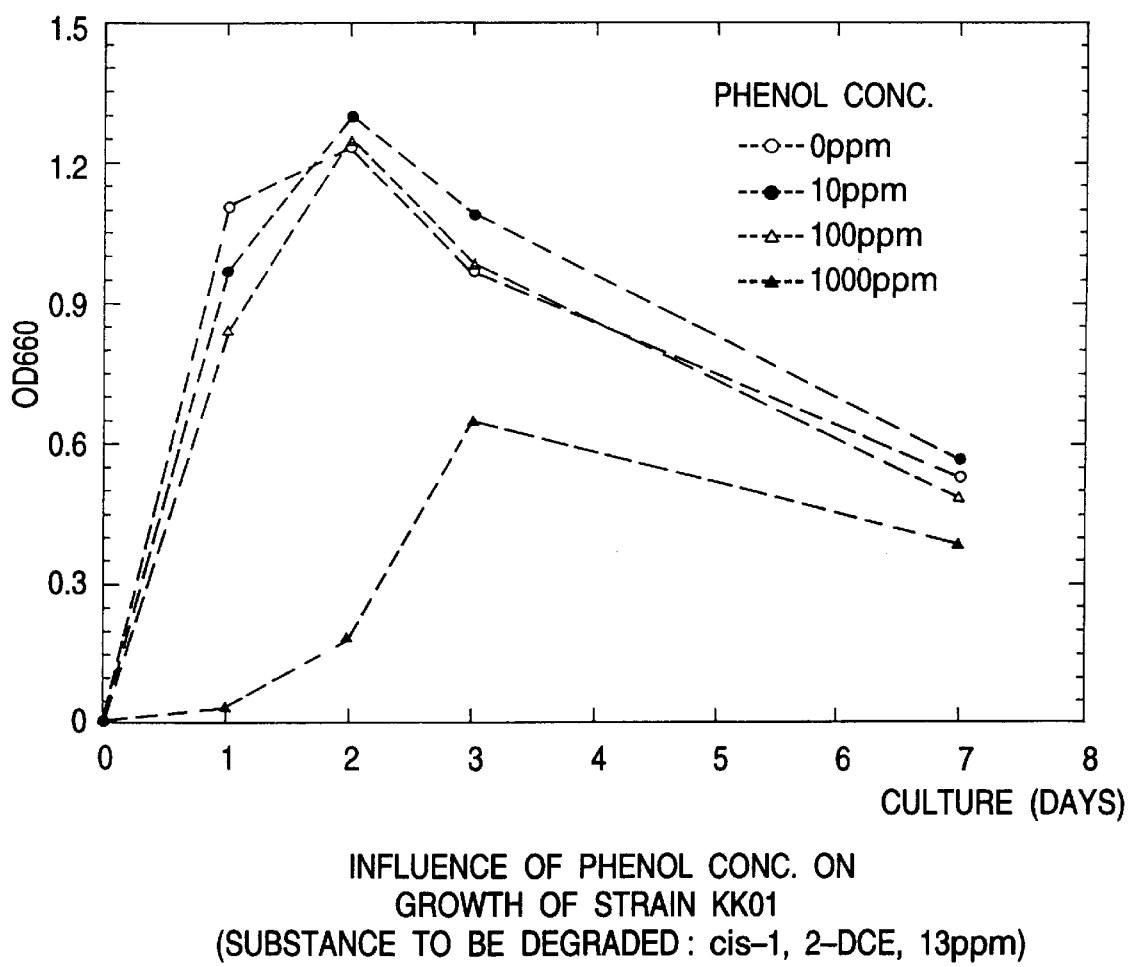
FIG. 33 shows the influence of phenol concentration on the growth of a strain KK01 in Example 33.

On the other hand, as shown in FIG. 33, with regard to initial bacteria growth characteristics, when the phenol concentrations were 0, 10 and 100 ppm, all of their initial growth curves showed a convex form. A maximum bacteria number O.D.=1.2–1.3 was obtained, and culture days taken to reach the maximum were two days, which was common in the cases of these phenol concentrations.

When the phenol concentration was 1,000 ppm, the growth of the bacteria were apparently hindered, and the maximum bacteria number O.D. was about 0.7 after 3 days.

Example 34

The same cultivation as in Example 28 was carried out except that phenol was replaced with p-cresol as a TCE degrading inducer. In this case, the concentration of TCE was set to 15 ppm, and the concentrations of p-cresol were changed to 0 ppm, 10 ppm, 100 ppm and 1,000 ppm so as to inspect the influence of the p-cresol concentrations. The obtained results are shown in FIGS. 34 and 35.

Figure 34:
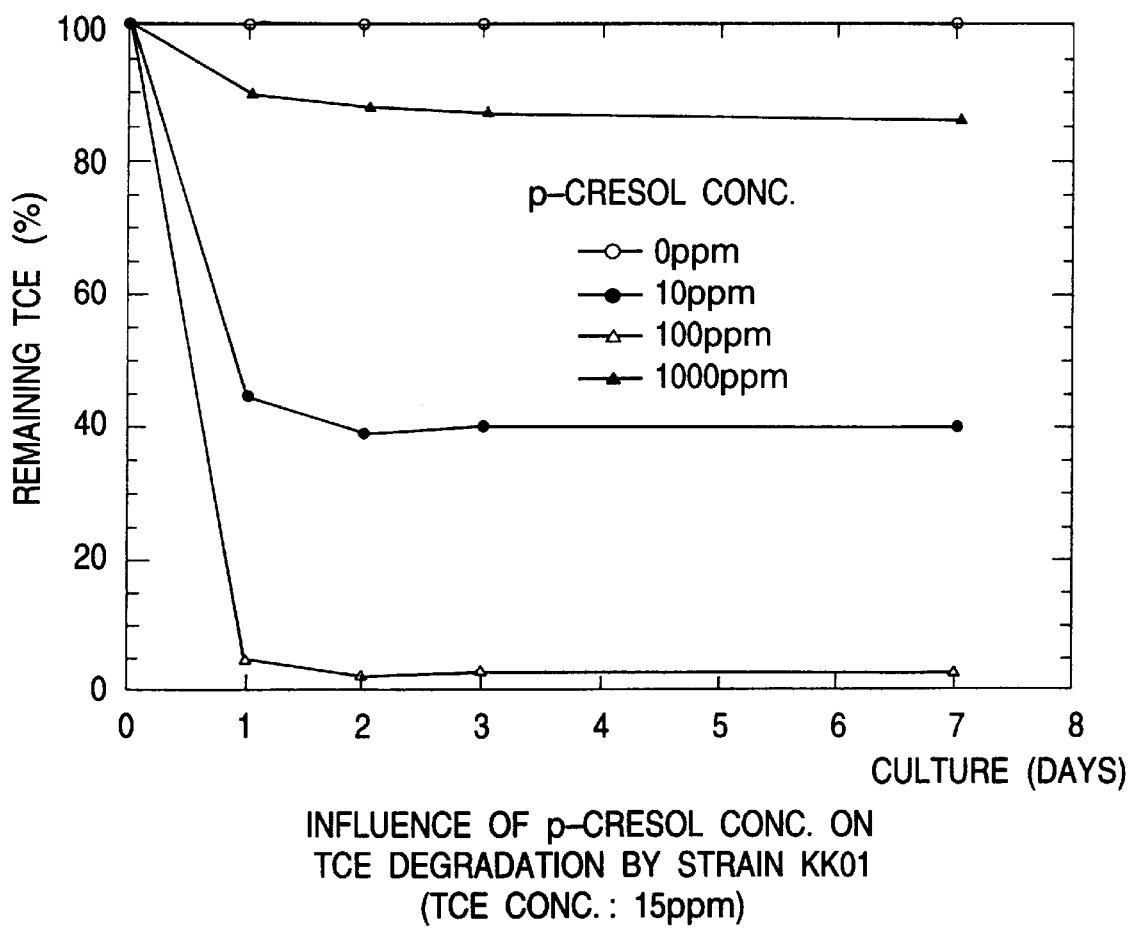
FIG. 34 shows the influence of p-cresol concentration on TCE degradation in Example 34.

As shown in FIG. 34, when the p-cresol concentrations were 100 ppm and 10 ppm, the degradations of TCE were 98% or more and at most 62% or so in two days, respectively. On the contrary, when the p-cresol concentration was 1,000 ppm, the TCE degradation was limited to about 14%.

Figure 35:
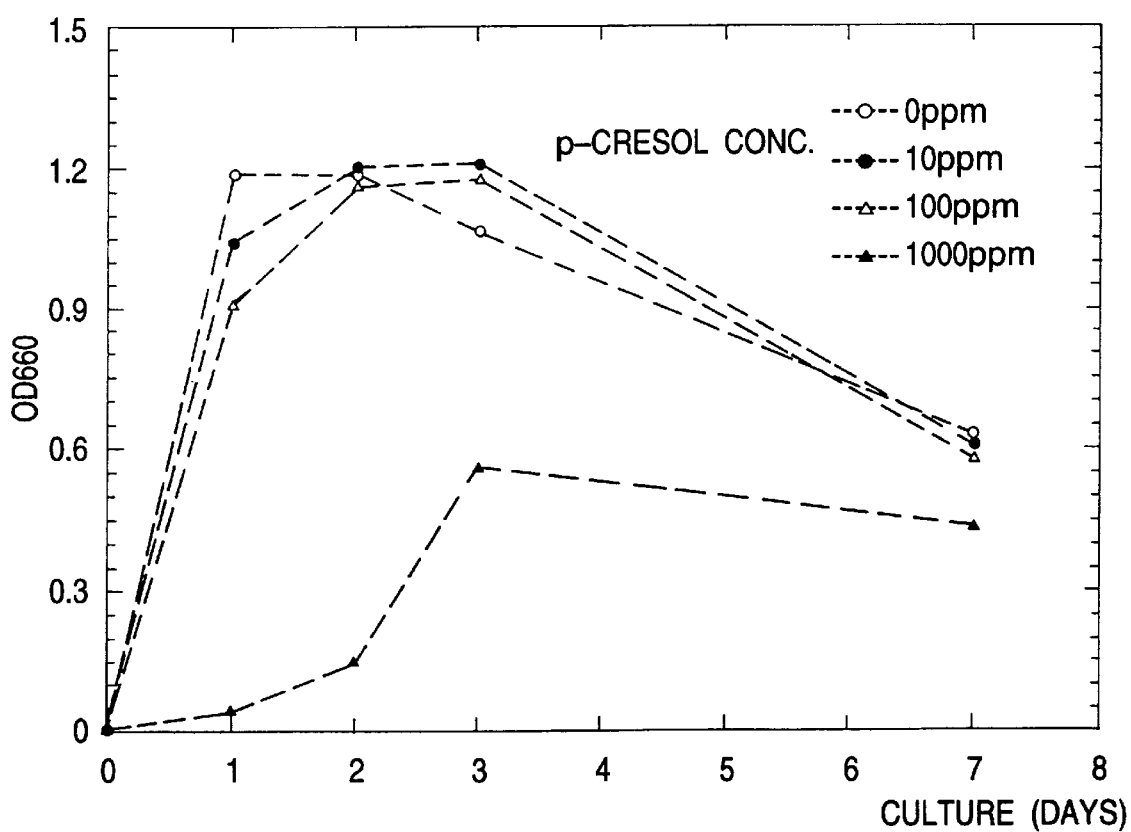
FIG. 35 shows the influence of p-cresol concentration on the growth of a strain KK01 in Example 34.

On the other hand, as shown in FIG. 35, in all the cases of p-cresol concentrations of 0, 10 and 100 ppm, initial bacteria growth characteristics could be represented by curves of a convex form. When the p-cresol concentration was 1,000 ppm, the bacteria growth was clearly hindered.

Example 35

Figure 36:
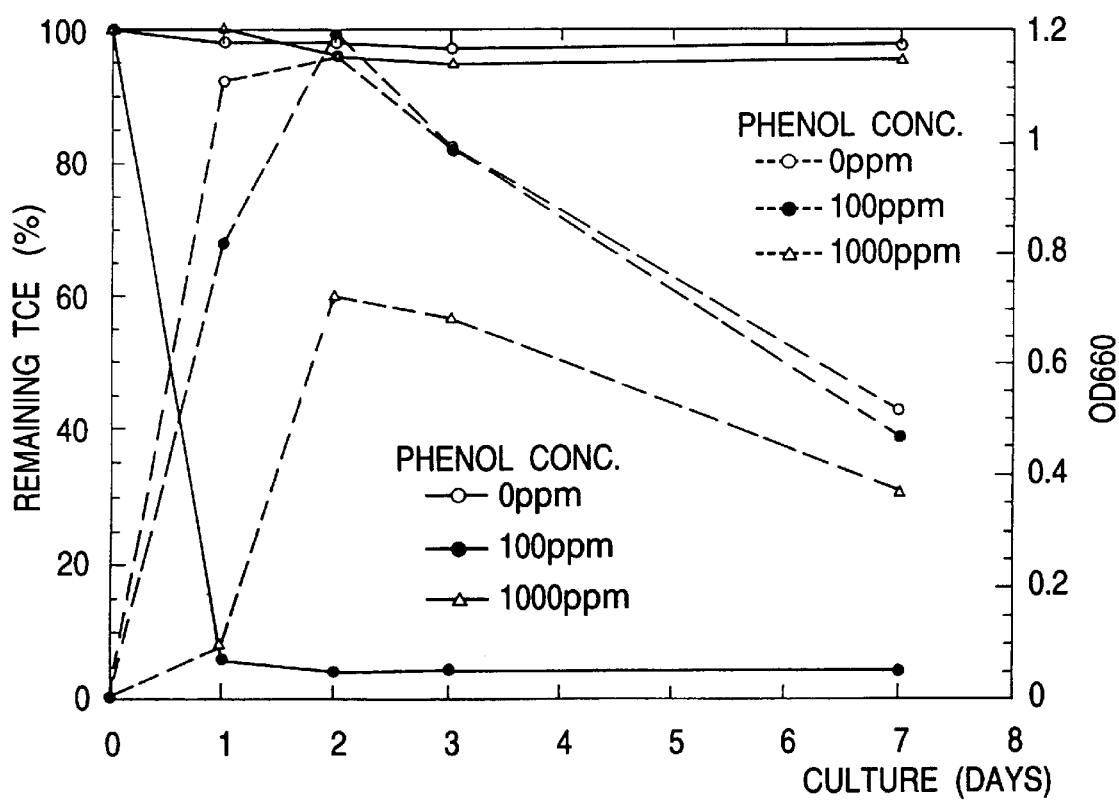
FIG. 36 shows the influence of phenol concentration on the growth of a strain BH and TCE degradation in Example 35.

An experiment was carried out by the same procedure as in Example 28 except that a *Pseudomonas putida* strain BH was used as TCE degrading bacteria. In this case, an M9 culture medium was used in which pH and TCE concentration were adjusted to 7.6 and 5 ppm, respectively. The results are shown in FIG. 36.

When a phenol concentration was 100 ppm, an initial bacteria growth curve showed a convex form, and at this time, TCE degradation proceeded about 95% in one day.

On the contrary, when the phenol concentration was 1,000 ppm, the bacteria growth was clearly hindered, and TCE was scarcely degraded.

Example 36

An experiment in comparing the trichloroethylene degrading ability in *Pseudomonas cepacia* strain KK01 (FERM BP-4235) regarding the present invention with that in Pseudomonas sp. strain G4 (ATCC 53617) was carried out in a manner as shown below.

*Pseudomonas cepacia* KK01 (FERM BP-4235) and Pseudomonas sp. G4 (ATCC 53617) were respectively cultured on an agar medium of MSB (basal salt medium) containing 0.05% of yeast extract and 100 ppm of phenol, wherein the MSB had the following compositions:

| | |
|---|---|
| $Na_2HPO_4 + KH_2PO_4$ (1 M, pH 6.8) | 40 ml |
| Huntner's vitamin-free mineral base | 20 ml |
| $(NH_4)_2SO_4$ | 1 g |
| distilled water | 840 ml |
| nitrilotriacetic acid | 10.0 g |
| $MgSO_4$ | 14.45 g |
| $CaCl_2.2H_2O$ | 3.335 g |
| $(NH_4)_6Mo_7O_{24}.4H_2O$ | 9.25 mg |
| $FeSO_4.7H_2O$ | 99 mg |
| Metals"44" | 50 ml |
| distilled water | |
| rest to make the total to be | 1000 ml |
| ethylenediaminetetraacetic acid | 250.0 mg |
| $ZnSO_4.7H_2O$ | 1095.0 mg (250 mg Zn) |
| $FeSO_4.7H_2O$ | 500.0 mg (100 mg Fe) |
| $MnSO_4.H_2O$ | 154.0 mg (50 mg Mn) |
| $CuSO_4.5H_2O$ | 39.2 mg (10 mg Cu) |
| $Co(NO_3)_2.6H_2O$ | 24.8 mg (5 mg Co) |
| $Na_2B_4O_7.10H_2O$ | 17.7 mg (2 mg B) |
| a few drops of sulfuric acid to prevent the formation of the precipitation distilled water | 100 ml |

Next, 200 ml of MSB liquid medium containing 0.2% of yeast extract were added to two 500 ml flasks respectively, followed by inoculating colonies of each kind of the strains grown on the agar mediums, and then conducting the shaking-culture at 30° C. for 20 hours.

Next, to a plurality of 27.5 ml vials, 10 ml MSB medium containing 8 ppm trichloroethylene, 0.05% yeast extract and 200 ppm phenol was added respectively, followed by grouping the vials in three groups consisting of Group I for the experiment of KK01 strain; Group II for the experiment of G4 strain; and Group III for control. 0.1 ml liquids containing the stain prepared in such shaking-culture was mentioned above were added respectively into Groups I and II vials, followed by sealing the vials with butyl rubber stoppers and aluminum sealing material and then conducting shaking-culture at 30° C. On the other hand, to the vial of Group III, only distilled water was added instead of such liquids containing the microorganism.

Figure 37:
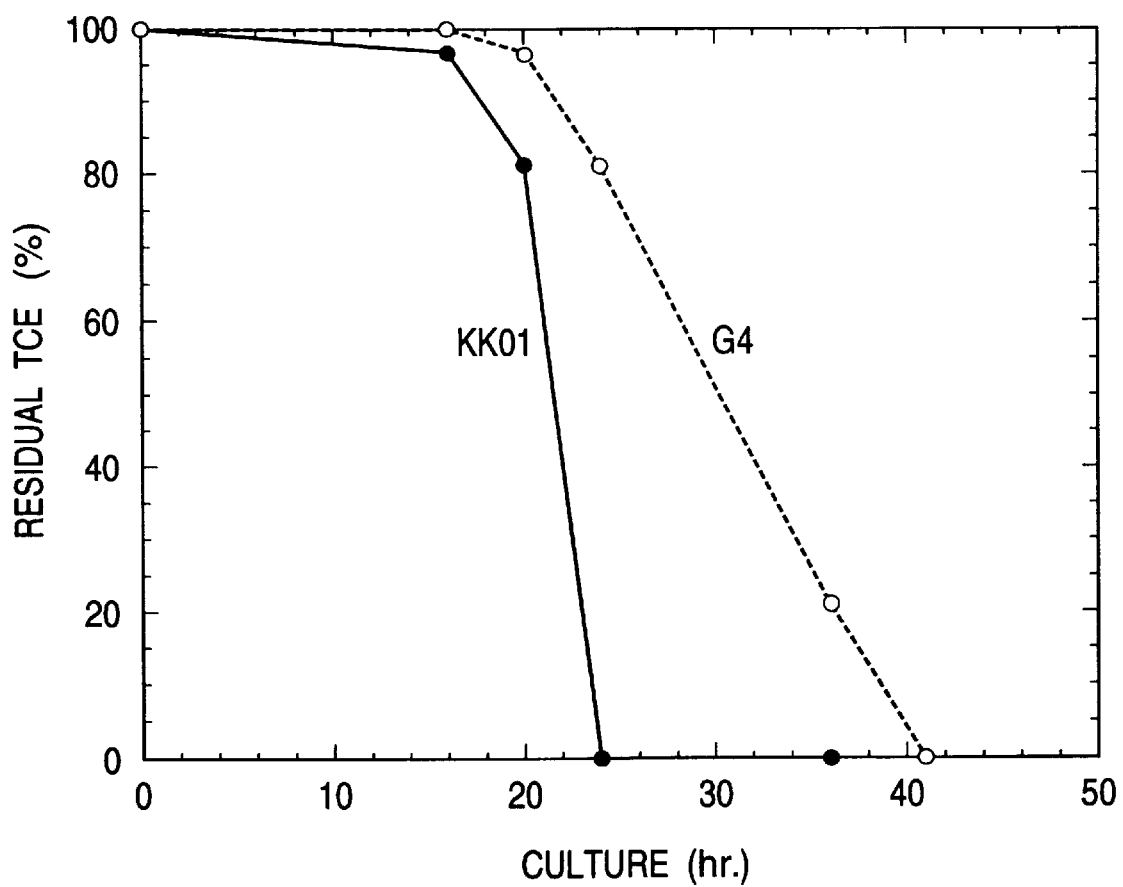
FIG. 37 shows the trichloroethylene degrading abilities in *Pseudomonas cepacia* strain KK01 and Pseudomonas sp. G4.

0.1 ml gas a sampling was collected from a head space of each vial of the Groups with the course of time, followed by measuring the concentration of trichloroethylene with gas chromatography (trade name: GC-14B manufactured by Shimadzu Corp.) (FID detector). FIG. 37 shows ratios of trichloroethylene concentration in the head space of Groups I or II vial to trichloroethylene concentration in the head space of Group III vial at each point of sampling times.

As shown in FIG. 37, *Pseudomonas cepacia* strain KK01 could almost completely degrade trichloroethylene of 8 ppm concentration in about 24 hours, which concentration deems to be high. In comparison with this, Pseudomonas sp. strain G4 did almost completely the same concentration of tricholoroethylene in about 41 hours. This result shows that *Pseudomonas cepacia* KK01 (FERM BP-4235) regarding the present invention has a remarkable ability of degrading trichloroethylene in comparison with Pseudomonas sp. strain G4.

The present invention has the following effects.

According to the present invention, a method for obtaining microorganisms having a TCE, phenolic compounds and furan compounds degrading ability from intestines of termites can be established, and this method permits obtaining the microorganism suitable for the biodegradation treatment of TCE contained in environment, such as waste water or the like.

Furthermore, by using the microorganisms obtained by the above-mentioned method, environment, such as waste water or the like containing at least one of TCE, phenolic compounds and furan compounds can be effectively remedied.

The present invention can provide a sufficiently practical method for remediating a soil by the utilization of the degradation of TCE compounds with the microorganisms in the soil.

The present invention also enables biological decomposition of various chemical substances such as trichloroethylene, phenolic compounds, furan compounds and the like using a single strain.

Additionally, according to the present invention, the concentration of an inducer for heightening a degrading activity per unit of the microorganisms for degrading chlorinated organic compounds can be estimated from initial growth characteristics of the bacteria, and so an effective biodegradation reaction showing the high degrading activity can be provided even under a small bacteria number.

What is claimed is:

1. A biologically pure culture of *Pseudomonas cepacia* strain KK01 (FERM BP-4235) which degrades trichloroethylene and a furan compound.

2. A method of obtaining a microorganism which decomposes a furan compound comprising the steps of:

isolating microorganisms dwelling in the intestine of a termite, culturing the microorganisms in a culture medium containing a furan compound as a sole carbon source, and isolating a colony grown in the culture medium, wherein the colony is Pseudomonas cepacia KK01 ( FERM BP4235).

3. A method of obtaining microorganisms which can decompose a furan compound according to claim 2, wherein said termite is *Nasutitermes takasaqoensis*.

4. A method of obtaining microorganisms which can decompose a furan compound according to claim 2, wherein said furan compound is at least one selected from the group consisting of furfural, tetrahydrofuran, furfuryl alcohol and cumaran.

\* \* \* \* \*

UNITED STATES PATENT AND TRADEMARK OFFICE
CERTIFICATE OF CORRECTION

PATENT NO.   : 6,096,530
DATED        : August 1, 2000
INVENTOR(S)  : Kinya Kato et al.

It is certified that error appears in the above-identified patent and that said Letters Patent is hereby corrected as shown below:

Column 3,
Line 60, "grown" should read -- grow --;

Column 4,
Line 47, "Xylosoxidsans" should be italicized;

Column 7,
Line 25, "method" should read -- a method --;

Column 13,
Line 12, "Pseudomonas cepcia" should be italicized;
Line 55, "0.05 t" should read -- 0.05% --;

Column 14,
Line 4, "takasaqoensis" should read -- takasagoensis --;
Line 52, "o.05 t" should read -- 0.05% --.

Column 15, Table 1,
Line 11, "ornithine:" should read -- ornithine: --.

Column 20,
Line 45, "above" should read -- above --;
Line 64, "takasaqoensis" should read -- takasagoensis --.

UNITED STATES PATENT AND TRADEMARK OFFICE
CERTIFICATE OF CORRECTION

PATENT NO. : 6,096,530  
DATED : August 1, 2000  
INVENTOR(S) : Kinya Kato et al.

Page 2 of 2

It is certified that error appears in the above-identified patent and that said Letters Patent is hereby corrected as shown below:

Column 23,  
Line 7, Close up right margin.  
Line 8, Close up left margin; and "Nasutitermes takasagoensis" should be italicized.

Column 30,  
Line 27, "takasaqoensis" should read -- takasagoensis --.

Signed and Sealed this

Twenty-seventh Day of November, 2001

Attest:

*Nicholas P. Godici*

NICHOLAS P. GODICI  
*Attesting Officer*   *Acting Director of the United States Patent and Trademark Office*